United States Patent [19]

Delgado et al.

[11] Patent Number: 5,349,052
[45] Date of Patent: Sep. 20, 1994

[54] PROCESS FOR FRACTIONATING POLYETHYLENE GLYCOL (PEG)-PROTEIN ADDUCTS AND AN ADDUCT FOR PEG AND GRANULOCYTE-MACROPHAGE COLONY STIMULATING FACTOR

[75] Inventors: Cristina Delgado; Gillian E. Francis; Derek Fisher, all of London, United Kingdom

[73] Assignee: Royal Free Hospital School of Medicine, London, United Kingdom

[21] Appl. No.: 60,889

[22] Filed: May 12, 1993

Related U.S. Application Data

[63] Continuation of Ser. No. 678,954, Apr. 19, 1991, abandoned.

[30] Foreign Application Priority Data

Oct. 20, 1988 [GB] United Kingdom ............... 8824591

[51] Int. Cl.$^5$ .................. C07K 3/08; C07K 3/12; C07K 15/06
[52] U.S. Cl. .................. 530/351; 530/410; 530/423
[58] Field of Search .................. 530/351, 410, 423; 424/85.1

[56] References Cited

U.S. PATENT DOCUMENTS

| | | | |
|---|---|---|---|
| 4,740,304 | 4/1988 | Tjerneld et al. | 210/639 |
| 4,766,106 | 8/1988 | Katre et al. | 514/12 |
| 4,904,584 | 2/1990 | Shaw | 530/351 |

FOREIGN PATENT DOCUMENTS

| | | |
|---|---|---|
| 0098110 | 1/1984 | European Pat. Off. . |
| 0154316 | 9/1985 | European Pat. Off. . |
| 0340741 | 11/1989 | European Pat. Off. . |
| WO89/05824 | 6/1989 | PCT Int'l Appl. . |
| WO89/06546 | 7/1989 | PCT Int'l Appl. . |
| 2193631 | 2/1988 | United Kingdom . |

OTHER PUBLICATIONS

Abuchowski et al., *J. Biol. Chem.* (1977) 252(11):3582–3586.
Karr et al, "Cell Separation By Immunoaffinity Partitioning With Polyethylene Glycol–Modified Protein A . . . ". J. Chromatography 442 (1988), pp. 219–227.
Chemical Abstracts, vol. 109, No. 9, Aug. 29, 1988, (Columbus, Ohio, US), L. Karr et al., "Cell Separation by Immunoaffinity Partitioning With Polyethylene Glycol–Modified Protein A in Aqueous Polymer Two–Phase Systems". Abstract No. 109:69845r.
Chemical Abstracts, vol. 90, No. 21, May 21, 1979, (Columbus, Ohio, US), A. Chaabouni et al., "Affinity Partition of Proteins in Aqueous Two–Phase Systems Containing Polyoxyethylene Glycol–Bound Ligand and Charged Dextrans", see p. 232, Abstract 164184x, & *J Chromatogr.* (1979) 171:135–143.

*Primary Examiner*—Jeffrey E. Russel
*Attorney, Agent, or Firm*—Morrison & Foerster

[57] ABSTRACT

The invention relates to fractionating a mixture of polyethylene glycol (PEG)-protein adducts having different degrees of PEG substitution by partitioning the PEG-protein adducts in a PEG-containing aqueous biphasic system according to the degree of PEG substitution. A new PEG-gm-CSF obtained by the process is useful in pharmaceutical compositions for use in therapeutic or diagnostic methods.

9 Claims, 15 Drawing Sheets

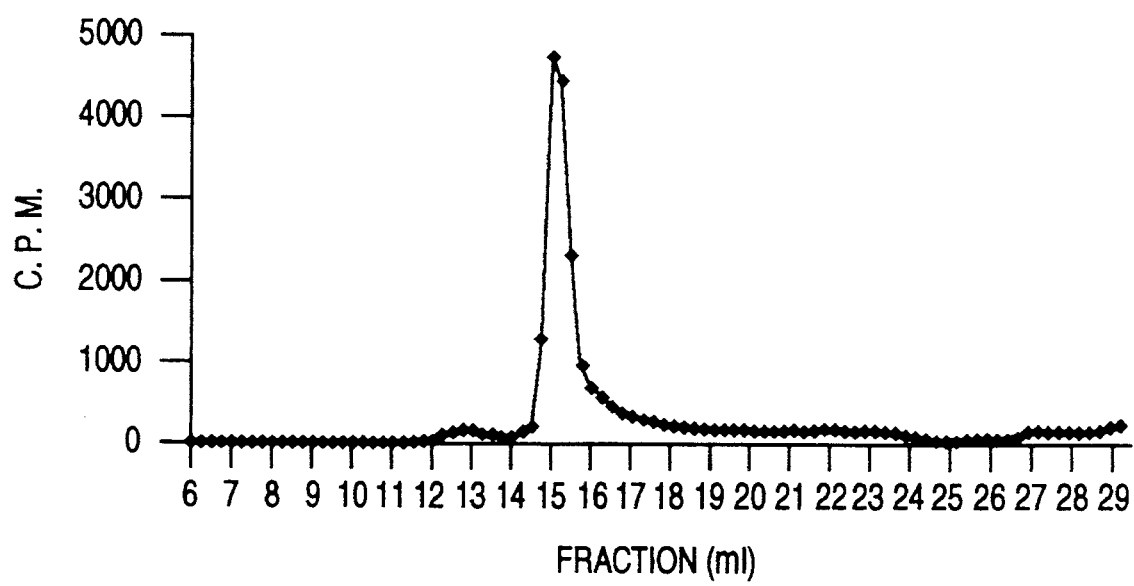
FIG. 7A.1.
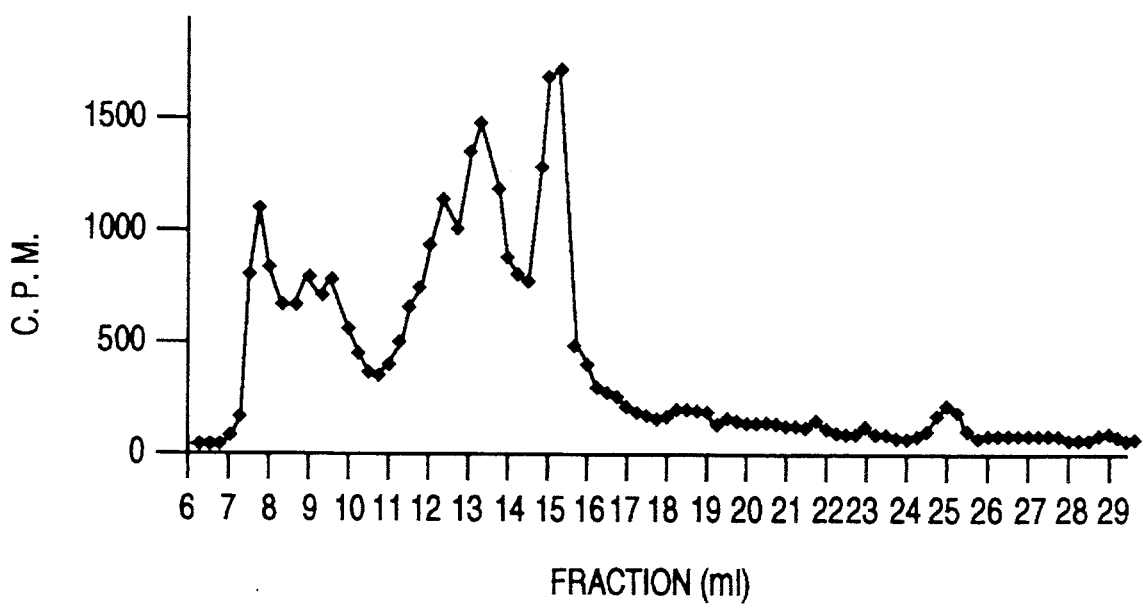
FIG. 7A.2.

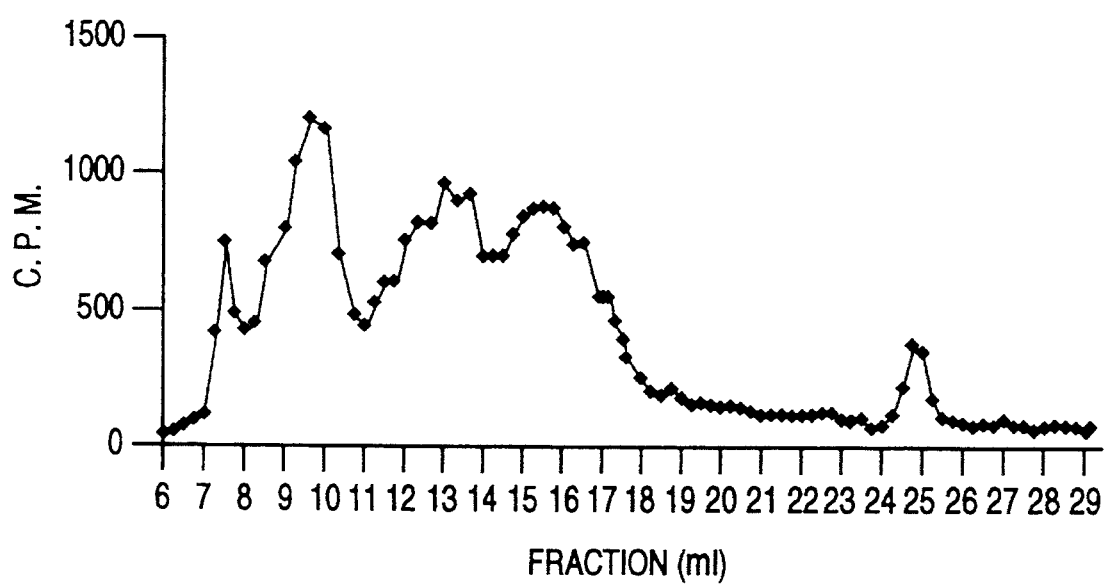
FIG. 7A.3.

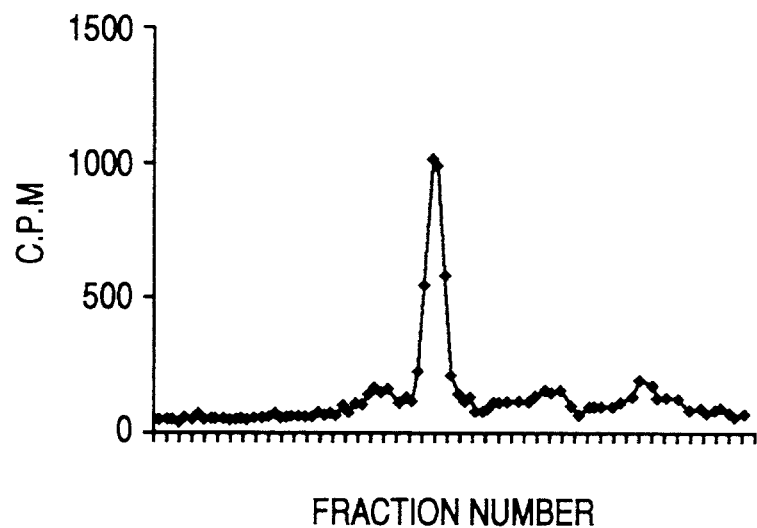
FIG. 7B.1.
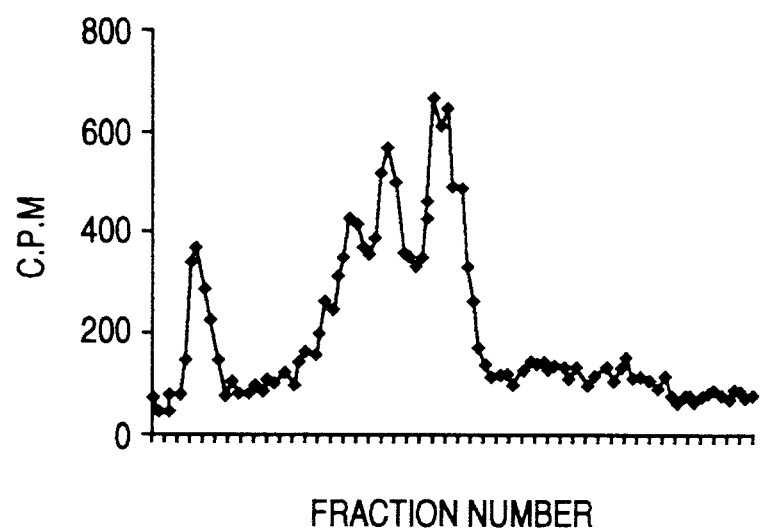
FIG. 7B.2.

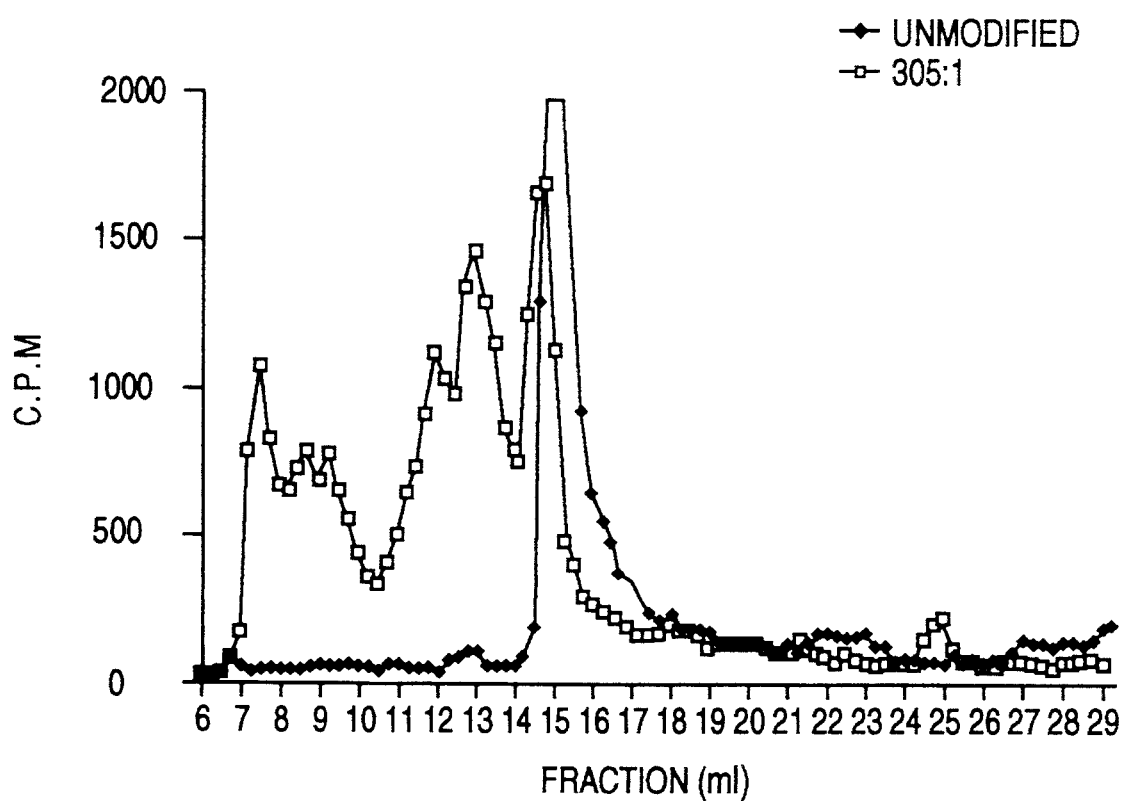
FIG. 8B.1.
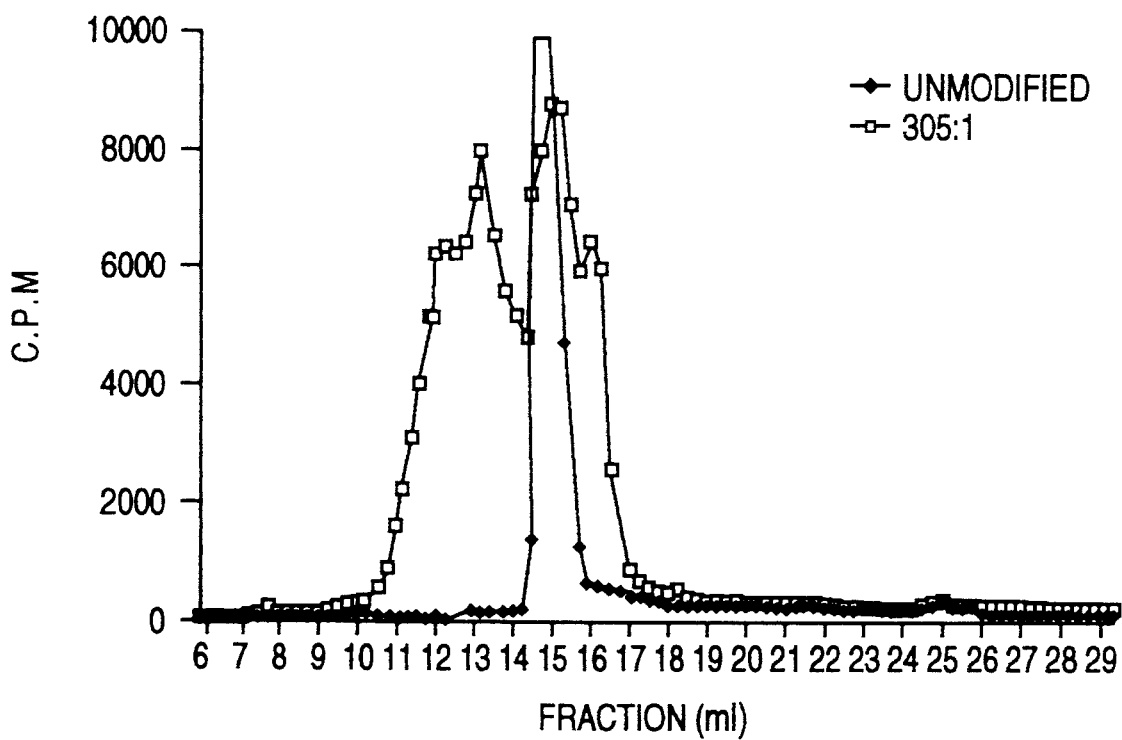
FIG. 8B.2.

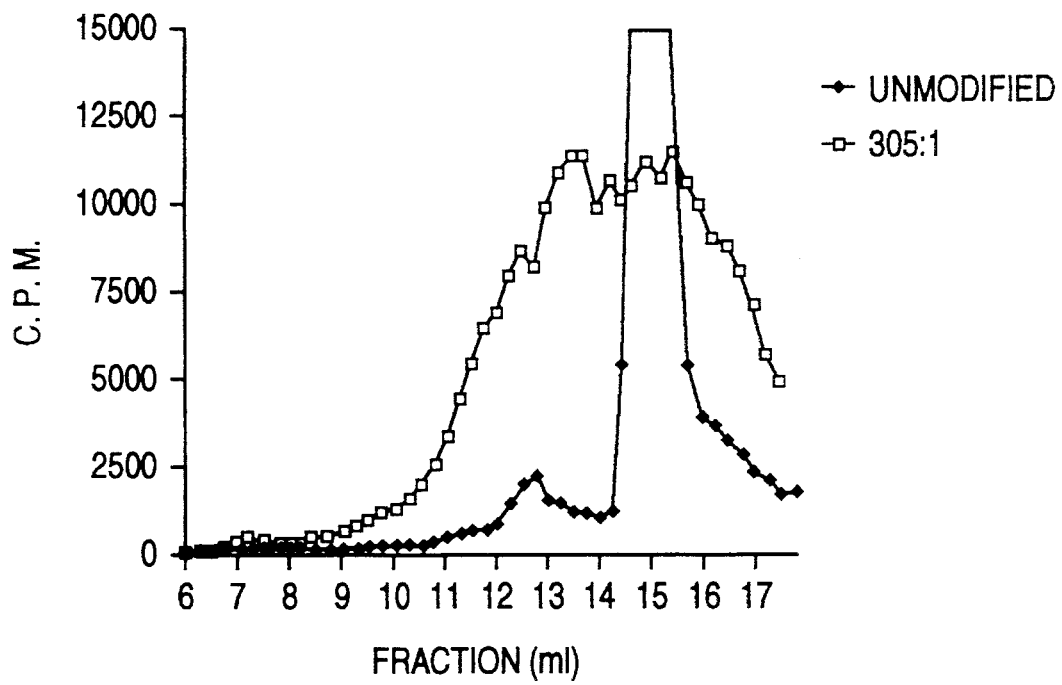
FIG. 8B.3.
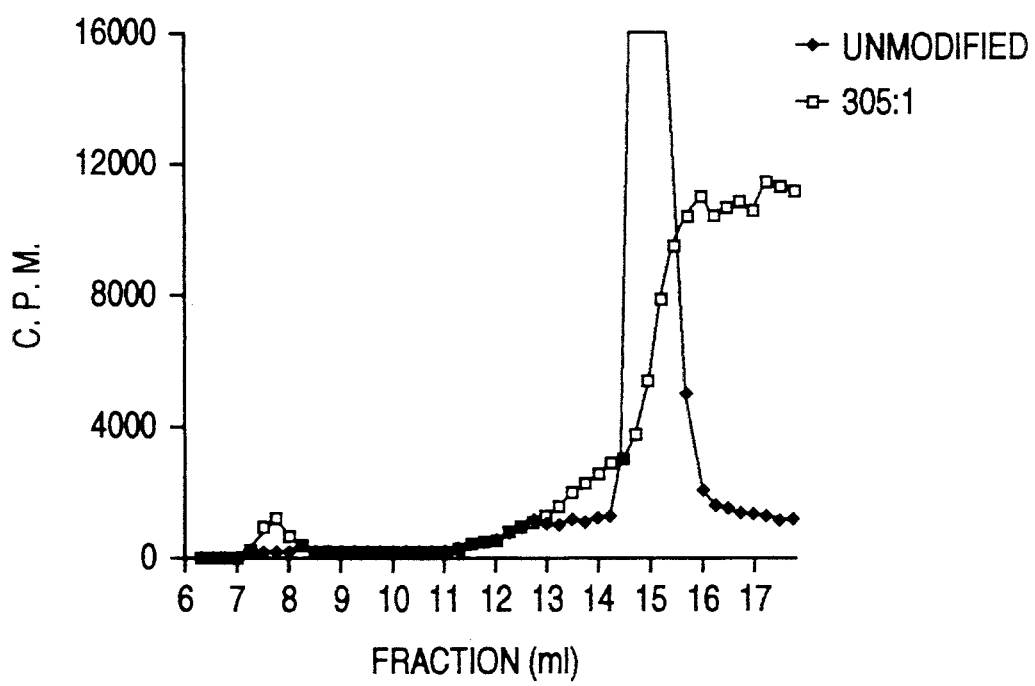
FIG. 8B.4.

PROCESS FOR FRACTIONATING POLYETHYLENE GLYCOL (PEG)-PROTEIN ADDUCTS AND AN ADDUCT FOR PEG AND GRANULOCYTE-MACROPHAGE COLONY STIMULATING FACTOR

This application is a continuation of application Ser. No. 07/678,954, filed Apr. 19, 1991, now abandoned.

The present invention relates to a process for fractionating polyethylene glycol-protein adducts.

Polyethylene glycol is a long chain, linear synthetic polymer composed of ethylene oxide units, $HO(CH_2CH_2O)_nCH_2CH_2OH$, in which n can vary to provide compounds with molecular weights from 200–20,000. It is non-toxic and has been administered orally and intravenously to humans (PEG-adenosine deaminase for severe combined immunodeficiency disease; PEG-asparaginase for acute lymphoblastic leukaemia; PEG-superoxide dimutase for oxygen toxicity (3-7)). PEG can be coupled to proteins following appropriate derivatisation of the OH groups of the PEG. The $NH_2$ groups of lysine side chains are particularly accessible sites and either few or many sites can be modified. Given adequate technology for their production, PEG-modified proteins have numerous therapeutic and other applications. Many proteins of potential clinical use have extremely short half lives necessitating administration by continuous infusion (an expensive, unpleasant and potentially hazardous procedure). PEG modification extends plasma half lives and has been used to increase the bio-availability of enzymes (see below). Reduction of antigenicity of proteins is also produced by PEG modification and this will extend their clinical use allowing more protracted administration. In addition, with proteins having pleiotropic biological effects, PEG modification creates products with a new spectrum of activities, because of differential loss of separate biological properties. With antibodies, for example, PEG modification dissociates antibody binding and complement fixing activities. PEG modification also alters biochemical and physical properties of proteins in ways that may increase their usefulness (e.g. increased solubility; increased resistance to proteolytic degradation; altered kinetics, pH and/or temperature optima and changed substrate specificity of enzymes). This covalent modification of proteins has a number of consequences:

(i) Increased plasma half-life: This has been found with numerous proteins (See Table 1 and reference 8-17) and has already been exploited clinically. Two children with adenosine deaminase deficiency were successfully treated with PEG-modified bovine adenosine deaminase (18). In acute lymphoblastic leukaemia, 74% of 20 patients achieved complete or partial remissions with PEG-asparaginase ( 5). Increased half-life and enhanced antitumour potency was also observed with PEG-interleukin 2 in the Meth A murine sarcoma model (19). The basis for this increase in half-life is not understood and may include such factors as reduction of glomerular filtration of small peptides because of the increase in size due to PEG modification (19). The increase in biological potency (which may relate to other phenomena in addition to the increased half-life) is potentially very important in the use of PEG-cytokine adducts as pharmacological agents in cancer therapy,

TABLE I

The known effects of linking PEG to proteins upon their circulation half lives.

| PROTEIN | ANIMAL | HALF LIFE native protein | (HOURS) PEG-protein | REFERENCE |
| --- | --- | --- | --- | --- |
| asparaginase | man | 20 | 357 | 8. |
| glutaminase-asparaginase | man | <0.5 | 72 | 9. |
| uricase | man | <3 | 8 | 10. |
| glutaminase-asparaginase | mouse | 2 | 24 | 11. |
| asparaginase | mouse | <6 | 96 | 12. |
| arginase | mouse | <1 | 12 | 13. |
| superoxide dismutase | mouse | 0.06 | 16.5 | 14. |
| lactoferrin | mouse | 0.05 | 1 | 14. |
| streptokinase | mouse | 0.07 | 0.33 | 15. |
| plasma-streptokinase complex | mouse | 0.05 | 0.22 | 15. |
| adenosine deaminase | mouse | 0.5 | 28 | 16. |
| asparaginase | rat | 2.9 | 56 | 17. | ii) Altered biochemical and physical properties: These include increased solubility (20), because of the addition of hydrophilic PEG chains (useful for proteins like interleukin 2 which have limited solubility at physiological pH (19)), increased resistance to proteolytic degradation (21), changes in kinetics or pH and temperature optima or substrate specificity of enzymes (10,20,22,23)). Relevant to the present project are observations which suggest differential effect on function e.g. complement fixing activity and antigen-binding are lost and retained respectively after PEG-modification of IgG (24). PEG-ribonuclease has an altered activity for high but not low molecular weight substrates (25). To some extent, these effects can be controlled by varying the number of sites on the protein modified and the length of the PEG polymer.

(iii) Reduced antigenicity: this includes reduced ability to react to antibodies to the unmodified protein and low immunogenicity of the PEG-proteins themselves (26).

Coupling of PEG to proteins is usually achieved by activation of the hydroxyl groups of PEG with a suitable reagent that can be fully substituted by nucleophilic groups in the protein (mainly lysine E-amino groups) (27). Cyanuric chloride has been the most widely used agent for activation of PEG and this requires a very basic pH for the subsequent coupling step with the protein to be modified (28,27). In order to avoid these adverse conditions (particularly important when dealing with labile proteins like growth factors), alternative methods have been sought. However, 1,1'-carbonyldiimidazole requires very long times for the coupling step (14) and using phenylchloroformates does not avoid the need for basic pH (25).

Although much of this information has been available for many years, PEG-proteins are not widely available commercially.

Tresyl chloride (2,2,2,-trifluoroethane-sulphonyl chloride) has proved useful for activating agarose and other solid supports carrying hydroxyl groups so that they may be coupled to proteins. The attraction of this method is that coupling to proteins takes place quickly and under very mild conditions (28,29). We have successfully applied this approach to the activation of monomethoxyPEG (MPEG), this has a single free derivatisable OH group. We have demonstrated the subsequent coupling of MPEG to both antibodies (30) and albumin (see example 1), under mild conditions (pH 7.5 phosphate buffer, at room temperature). An advantage over previous techniques is that the reaction mixture is innocuous and does not have to be removed before the PEG-protein is used. We have also developed a technique to neutralise excess tresyl-PEG after the coupling step (to prevent reaction with other proteins and/or cells) thus avoiding the need for laborious chromatography or ultrafiltration to remove it. These improvements are of importance when applying the method to labile growth factor proteins, which are notoriously sensitive to manipulations such as ultrafiltration.

Given acceptable (non-denaturing) conditions for the coupling step, there are two main variables that will affect the biological properties of the PEG-proteins and these may be controlled in the manufacturing process. One is the length of the PEG molecules attached per protein molecule and the second is the number of PEG molecules per protein.

Where proteins have several lysine groups, varying the molar ratio of activated MPEG to protein influences the degrees of substitution markedly (see example 2). What is needed is a means of determining what degree of substitution gives the best outcome visa vis the desired biological properties and then to devise a manufacturing scheme which best achieves this degree of substitution. Biochemical monitoring methods are cumbersome (2) and do not give an estimate of the variability in substitution of the population of modified protein molecules. They also do not allow recovery of materials with different degrees of substitution (the latter is difficult to control by altering molar ratios, since a wide distribution of degrees of substitution is observed at any given molar ratio, until full substitution is approached at high molar ratios (see example 2). Both analytical work to determine which degree of substitution produces the optimum effect and the manufacturing process require a means of fractionating peptides/proteins with different (and preferably precisely defined) degrees of substitution. The problem is likely to be widespread since most clinically useful proteins have several lysine residues (Table II).

TABLE II

| Growth Factor | Lysine Residues | Total Amino Acids |
| --- | --- | --- |
| Interleukins: | | |
| Interleukin 1 | 19 | 271 |
| Interleukin 2 | 10 | 153 |
| Interleukin 3 | 9 | 166 |
| Interferons: | | |
| gamma | 20 | 146 |
| fibroblast (beta) | 11 | 166 |
| leukocyte (beta) | 8 | 166 |
| G-CSF | 4 | 178 |
| GM-CSF | 6 | 144 |

Although PEG-modification of over a dozen proteins has now been described, frequently in extensive practical detail, little attention has been given to the PEG-proteins being heterogeneous in their degree of substitution with PEG (23).

The partitioning behaviour of PEG-protein adducts in PEG-containing aqueous biphasic systems has not been previously defined, nor has the relationship between degree of PEG substitution and partitioning coefficient. On investigating the partitioning behaviour in such systems we have surprisingly discovered that PEG-containing aqueous biphasic systems are uniquely tailored to separating PEG-proteins sensitively and can thus be used to monitor the effect of degree of modification on biological properties and, on a bulk scale, to prepare PEG proteins of specified degrees of substitution.

The invention therefore provides a process for fractionating a mixture of PEG-protein adducts comprising partitioning the PEG-protein adducts in a PEG-containing aqueous biphasic system. Preferably the process further comprises the step of recovering a PEG-protein adduct of predetermined degree of PEG substitution from one phase of the biphasic system. Whilst any PEG protein adduct mixture may be fractionated in accordance with the invention, it is preferred to use adducts of monomethoxyPEG preferably those formed by reaction of the protein with tresyl monomethoxyPEG, (TMPEG). In a particular aspect of the invention, unreacted TMPEG is destroyed or the adduct-forming reaction is quenched, by addition of lysine or albumin. Partitioning may be performed batchwise or continuously, for instance by counter currents of the two phases and may be repeated to obtain additional fractionation.

BRIEF DESCRIPTION OF THE DRAWINGS

FIG. 7A1 (upper panel) shows FPLC of unmodified recombinant human gm-CSF-$^{125}$I.

FIG. 7A2 (middle panel) shows FPLC of recombinant human gm-CSF-$^{125}$I exposed to TMPEG:lysine at a molar ratio of 305:1.

FIG. 7A3 (lower panel) shows FPLC of recombinant human gm-CSF-$^{125}$I exposed to TMPEG:lysine at a molar ratio of 1000:1.

FIG. 7B1 (upper panel) shows FPLC of a different batch of recombinant human gm-CSF-$^{125}$I exposed to TMPEG:lysine at a molar ratio of 10:1.

FIG. 7B2 (lower panel) shows FPLC of recombinant human gm-CSF-$^{125}$I exposed to TMPEG:lysine at a molar ratio of 305:1.

FIG. 8B1 (upper panel) shows the result of FPLC of recombinant human gm-CSF-$^{125}$I PEGylated with 13 week old TMPEG (stored at room temperature under desiccation).

FIG. 8B2 (lower panel) shows the result of FPLC of recombinant human gm-CSF-$^{125}$I PEGylated with 17 week old TMPEG (stored at room temperature under desiccation).

FIG. 8B3 (lower panel) shows the result of FPLC of recombinant human gm-CSF-$^{125}$I PEGylated with 19 week old TMPEG (stored at room temperature under desiccation).

FIG. 8B4 (cont). (lower panel) shows the result of FPLC of recombinant human gm-CSF-$^{125}$I PEGylated with 21 week old TMPEG (stored at room temperature under desiccation).

Figure 1:
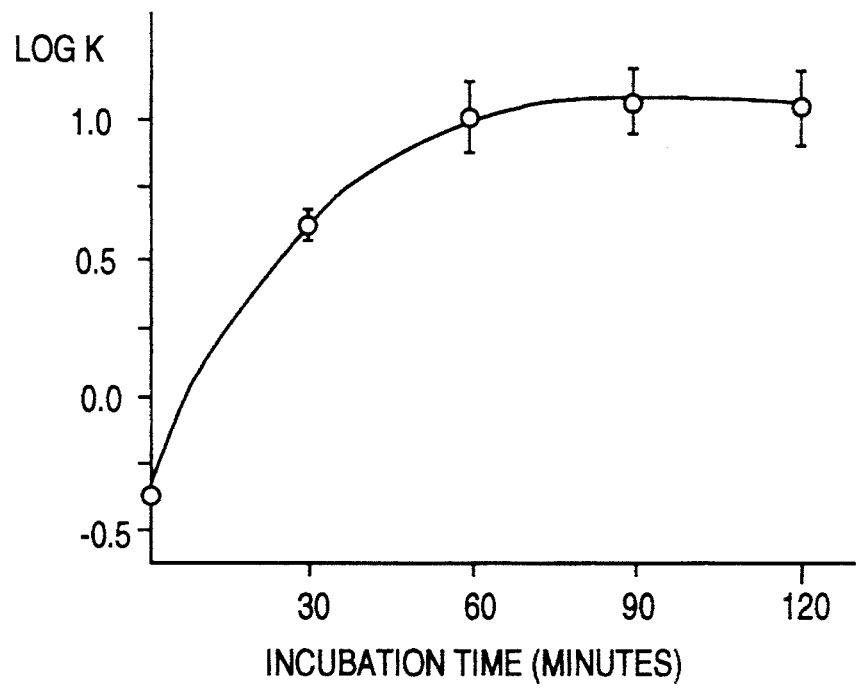
FIG. 1 is a graph showing Log K versus incubation time for BSA incubated with TMPEG.

The analysis of the extent of modification (molar ratios) of PEG to protein.

We have established using phase partitioning in an aqueous biphasic system of PEG and dextran that there is a linear relationship between log of partition coefficient of PEG-proteins and the number of amino acids coupled to PEG. This relationship has not, as far as we are aware, been established before and although a log linear relationship was predicted, there is a significant departure from the theoretical predicted behaviour. The parameters of the regression are not those predicted on the basis of the partitioning behaviour of the two components. This discovery is therefore not implicit in prior work. The basis of the method is that coupling PEG to proteins naturally increases affinity for the PEG-rich upper phase and hence increases the partition coefficient (concentration in top phase/concentration in bottom phase). The exponential nature of this relationship makes partitioning a very sensitive method with which to monitor modification. This invention is described in detail in Example 1 below. The equation for the regression is also used to analyse the heterogeneity of substitution of the protein preparation and to define the extent of substitution present in individual fractions.

Surprisingly, this relationship does not hold for all PEG-modified proteins. With some there is a complex relationship between the log of partition coefficient and modification. This discovery is not implicit in prior work. This observation could be based on many factors, including aggregation, denaturation and concomitant change in surface properties, and change in isoelectric point. Without wishing to be bound by theory, this result (see Example 3) emphasises the need for analytical phase partitioning as a prerequisite to use of phase partitioning to fractionate PEG modified proteins.
Methodology for the analysis of the heterogeneity of modification (i.e. the range of PEG molecules per protein molecule) produced under individual reaction conditions.

Using phase partitioning in conjunction with counter current distribution to perform serial transfers on the PEG-modified protein discriminates between proteins that have been modified homogeneously or heterogeneously. Homogeneously modified proteins have identical partition coefficients whereas we have shown that for heterogeneously modified proteins there is an increment in partition coefficient over the range of fractions that contain the protein. Using the equation based on the analysis of method 1 the degree of substitution in individual fractions can be calculated, and the heterogeneity of the sample prepared at given molar ratios can be characterised. This method has not, as far as we are aware previously been applied to demonstrate the heterogeneity of substitution of PEG-protein adducts. The details of this method are given in Example 2 below.
Separation of proteins and/or peptides modified to different extents.

Given the considerable spread of the degree of substitution obtained at given (subsaturating) molar ratios in the coupling step, it is necessary to examine the relationship between substitution and the biological properties of the proteins (both desired and undesired) to determine at which PEG-protein ratio the optimal function of the protein is achieved. This may need to be performed as a matrix varying the length of PEG as well as the degree of substitution.

This method uses preparative-scale phase partitioning in conjunction with countercurrent distribution to fractionate PEG-proteins substituted to different degrees by PEG.

Having established which partition coefficient relates to optimal protein properties, preparative phase partitioning (with or without countercurrent distribution) can then be used to fractionate proteins with the desired degree of substitution. This may be necessary in the manufacturing process, if the degree of substitution is critical to obtaining optimal biological properties and if a sufficiently precise degree of substitution cannot be achieved by altering the reaction conditions for PEG coupling.

Uses of the Process i) Preparation of PEG-proteins adducts for clinical use

Genetically engineered proteins have many potential clinical roles and we cannot therefore give extensive examples here. PEG has been used to modify many classes of proteins including enzymes, antibodies, peptide hormones, growth factors, and cytokines. The increasing production of proteins for clinical use using recombinant DNA techniques greatly increases the availability of such proteins for clinical and other uses. The haematopoietic growth factors, for example, have a dramatic effect in reducing the cytopenias induced by chemo- and radiotherapy (31-33). Differentiation factors and cytokines are also showing promise in the therapy of neoplasia, both through direct anti-tumour effects and by modulating host response (reviewed in 4,5). Bio-active peptides are also undergoing clinical trials and the use of peptide hormones (e.g. insulin) is well established.

There are, however, limitations to the use of these proteins which can be solved by the manufacture of suitable PEG-protein adducts. The first is that they are rapidly cleared and thus often require continuous infusion. They are also expensive to produce and thus in limited supply, particularly in the early stages of development. Antigenic and physical or biochemical properties of the proteins may also be undesirable (as mentioned above). In addition some factors have pleiotropic actions which if modified independently produce proteins with new potential clinical uses. For example, some factors are potent differentiation inducers but also have a growth stimulating effect which makes them unsuitable for use in differentiation therapy of malignancy, in their native state. Production of a PEG-protein adduct retaining only one of these properties produces a new factor with a different range of clinical uses.

The methods described allow analysis of the relationship between PEG-protein ratios and biological properties so that the best ratio of substitution can be selected. The analytical method also gives essential information for the design of a preparation scheme for manufacturing and/or fractionating PEG-protein adducts of the desired degree of substitution (i.e. with the desired biological properties).

ii) As a Research Tool

The method also has potential research applications. By analysing the way in which varying the degree of substitution by PEG influences the biological properties of the protein, the range of substitutions which promotes (or inhibits) a specific property can be established. Using the preparative method to prepare a series of fractions of varying degrees of substitution one can then establish biochemically (for example by peptide mapping) the locations of the amino acids modified at the various degrees of substitution. This will vary as the molar ratio in the coupling step is increased with the most to the least readily modified acceptor site. This will allow determination of which locations on the protein are associated with individual biological properties.

THE INVENTION IS ILLUSTRATED IN THE FOLLOWING EXAMPLES

All reagents used were ANALAR grade. In the specific products origin is indicated.

Preparation of Tresylated Monomethoxypolyethylene Glycol (TMPEG)

To avoid hydrolysis of tresyl chloride, all reagents were dried before use.

a) Drying Monomethoxypolyethylene Glycol

MPEG (Mr 5000, Union Carbide, U.S.A. was dissolved in benzene (B.P. 79–80° C.) and the water-organic azeotrope (B.P. 65° C.) was distilled off. MPEG was recovered by removal of solvent under reduced pressure, and was finally dried by leaving overnight at room temperature under vacuum.

b) Drying Dichloromethane

Dichloromethane (ANALAR from British Drug House, Poole, U.K) was dried over molecular sieve A3 (100 g per liter of solvent) overnight at room temperature.

c) Activation of MPEG with Tresyl Chloride

Activation of MPEG-5000 with tresyl chloride was carried out using a molar ratio of tresyl chloride to available hydroxyl groups in MPEG of 2.5:1.

Dry MPEG (18 g. 3.5 mmol) was dissolved in dry dichloromethane (45 ml) at room temperature. The mixture was cooled to 0° C., stirred magnetically and 1.125 ml (14 mmol) pyridine (BDH, U.K.) and 1 ml (9 mmol) of tresyl chloride (Fluka AG, Switzerland) at 0° C. were added dropwise. The reaction was allowed to continue at room temperature with constant stirring for 1.5 hr before the dichloromethane was removed by evaporating under reduced pressure. The white solid was dried under vacuum overnight at room temperature.

d) Washing the TMPEG

TMPEG was suspended in methanol-HCL mixture ( 250: 1 ) and allowed to precipitate at −20° C. for 8 hr. The white solid produced was collected at 0° C. and the filtrate checked for pyridine content (255 nm). This procedure was repeated by using methanol-HCl (1000: 1) as washing mixture until no pyridine could be detected. Finally, the pyridine free TMEG (12–14 g; 65–75% yield) was dried under vacuum for several hours at room temperature.

The sulphur content of the white solid obtained was 0.5%. Theoretical content of 1 tresyl group per molecule of MPEG is 0.62% considering an average molecular weight of 5000 for the activated polymer. Therefore, approximately 80% of hydroxyl groups in the MPEG were transformed into tresyl esters.

Tresylated MPEG was shown to be stable when stored at room temperature up to 3 months. TMPEG samples taken from one batch of the product at different times since the production were reacted with BSA. The product MPEG-BSA was analysed by partitioning in aqueous PEG-dextran two-phase systems. Partition coefficients, K, of MPEG-BSA samples obtained during that period were within the range 0.9–1.2 (Log K) indicating stability of the TMPEG preparation.

e) Coupling of TMPEG to Protein

Bovine serum albumin (98–99% Sigma Chemical Co (U.S.A.) was used. Coupling was carried out at room temperature in sodium phosphate buffer (pH 7.5) containing sodium chloride (see details in the legend for each figure). Appropriate volumes of protein and TMPEG solutions made up in the correponding coupling buffer were mixed and left under gentle stirring at room temperature. At intervals samples were withdrawn and analysed as described below.

f) Analysis of Native and MPEG-modified Protein i) Primary amino groups in native albumin were estimated by the sodium trinitrobenzene sulphonate (TNBS) method in which the UV absorption of the TNBS-primary amine conjugate is measured (36). Since PEG interferes with this method, the primary amino groups in PEG-modified albumin and unmodified control were determined by the fluorometric assay described by Stocks et al (37).

ii) Partition coefficients of both native and MPEG-modified albumin were measured at 25° C. in single tubes containing 1 g of a two-phase system of 4.75% (w/w) PEG-6000 (Lot 9159110, BDH, UK), 4.75% (w/w) Dextran-T500 (Dx) (Lot 38624, Pharmacia, Sweden), 0.01M sodium phosphate buffer pH 6.8, 0.15M sodium chloride. The phase system was prepared from stock solutions of 40% PEG, approx. 20% Dextran (standardised by polarimetry), 0.44M sodium phosphate buffer pH 6.8 and 0.6M sodium .chloride. Albumin and albumin coupled to MPEG were incorporated into the phase system by replacing 0.1 g of the water used to phases by 0.1 g of solutions of albumin and PEG-albumins in the coupling buffer.

After mixing 30-40 times by inversion the mixture was left to settle until complete separation of the phases was achieved. Aliquots from top and bottom phases were analysed for protein concentration. The partition coefficient is the ratio of protein in the top and bottom phases.

iii) Protein concentration was measured by Coomassie Brilliant Blue assay (38). This assay has been demonstrated to detect low concentrations of proteins and is not subject to any interference with either PEG or Dextran, such as occurs with the Lowry method (39).

(iv) Counter-current distribution

Counter-current distribution (CCD) of albumin and MPEG-modified albumin was carried out in a phase system formed by 4.75% (w/w) PEG, 4.75% (w/w) Dx and 0.15M sodium chloride buffered with 0.01M sodium phosphate pH 6.8. The phase system was prepared by mixing required quantities of 40% (w/w) PEG-6000 (Lot 9159110, BDH, UK), 20% (w/w) Dx-T500 (Lot MI 02434, Pharmacia, Sweden), 0.6M sodium chloride, 0.44M sodium phosphate buffer pH 6.8 and distilled water. Once the top and bottom phases had separated at 25° C. the phases were stored until required.

An automatic thin-layer counter-current distribution apparatus BIOSHEF TLCCD MK2 constructed at the University of Sheffield (UK) was used (40). The distribution rotor consists of 60 cavities which were filled as follows: 0.823 ml of bottom phase and 0.823 ml of top phase were loaded into cavities 2 to 30 and 32 to 60. Cavities 1 and 31 were filled with 0.823 ml of bottom phase and 0.823 ml of top phase of biphasic system containing sample. This was prepared from the same stock solutions as the bulk system but replacing the distilled water by a solution containing the relevant protein and was made up immediately before running the experiment. The settling time was 7 min and the shaking time was 25 secs.

After completion of 30 transfers at room temperature, the contents of each cavity was collected directly into plastic tubes. Contents of each alternate cavities were diluted with 0.8 ml of 0.15M sodium chloride buffered with 0.01M sodium phosphate pH 6.8 to break the phase system. Protein concentration was then measured by the Bradford assay to obtain the distribution profile. The remaining tubes, which still contained two phases were used to determine the partition coefficients of the protein by measuring the protein concentrations in the top and bottom phases.

EXAMPLE 1

MODIFICATION OF ALBUMIN WITH MPEG AND PARTITIONING BEHAVIOUR OF THE COMPLEX MPEG-BSA

BSA was chosen as a well-characterised protein with 60 lysyl residues per molecule (41). The BSA powder supplied by Sigma showed 61±6 (n=12) amino groups per molecule and therefore, was used without purification.

The protein was incubated with TMPEG at room temperature in 0.2M sodium phosphate buffer pH 7.5 containing 0.5M sodium chloride. The final concentration of BSA was 1.5 mg/ml and the molar ratio TMPEG to lysyl residues was 16 to 1. Partition coefficient, K, of the protein was measured after 30,60,90 and 120 min of incubation. As it is shown in FIG. 1, K increases as the incubation of BSA and TMPEG proceed for the first hour and then reaches a "plateau". The increase in K indicates that the MPEG has been linked to the BSA; the surface of the protein become more PEG-like and as a consequence is directed towards the PEG-rich top phase of the biphasic system. This is an example of affinity partitioning extensively described elsewhere (42,43). We have observed that BSA incubated with ordinary MPEG did not increase its partition coefficient (data not shown). Therefore, it is possible to state that the increase in partition coefficient (FIG. 1) is due to a covalent linkage of the MPEG to the protein rather than to an adsorption of the polymer onto the protein. The constant K value obtained for the MPEG-BSA complex beyond 1 hr of incubation (FIG. 1) demonstrates the maximum change in K that can be achieved and probably indicates saturation of available PEG-binding sites.

Figure 2:
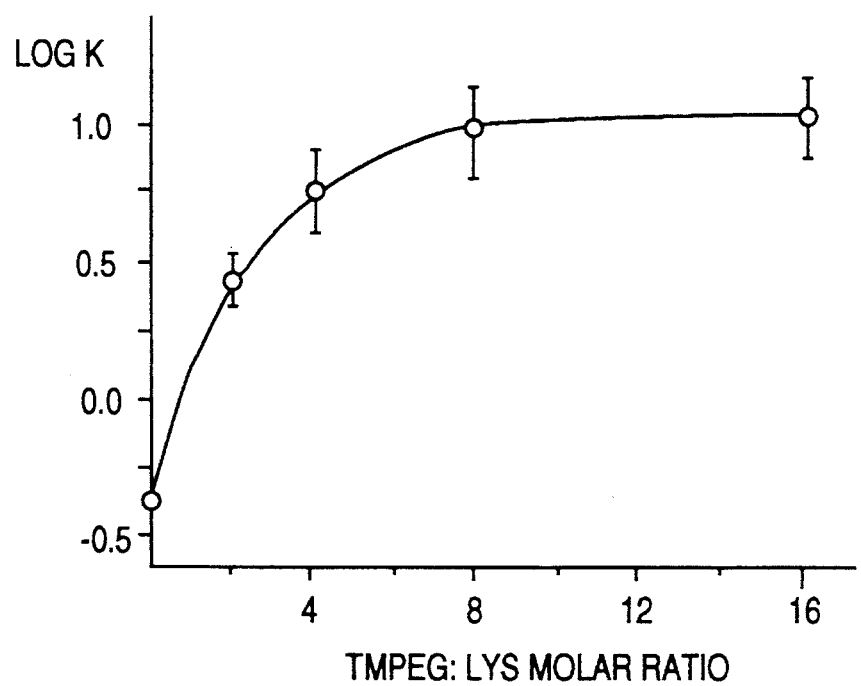
FIG. 2 is a graph of Log K versus TMPEG: Lys molar ratio for PEGylated BSA.

In order to construct PEG-protein adducts with varying degrees of substitution, we investigated the influence of the molar ratio TMPEG to BSA (lysyl residues) in the formation of the complex MPEG-BSA. An incubation time of 2 hrs was used. As shown in FIG. 2 an increase in the molar ratio TMPEG to lysyl groups up to over the range 2:1 to 16:1 leads to a progressive increase in the partition coefficient of the BSA.

Relationship Between Partition Coefficient and Degree of Modification

Partitioning in aqueous two-phase systems provides a means of analysing qualitatively and quantitatively the coupling of TMPEG to albumin without requiring any purification of the complex MPEG-albumin (see material and methods). This is of considerable advantage over other methods in which the adduct MPEG-protein must be separated from the unreacted MPEG (44).

Figure 3:
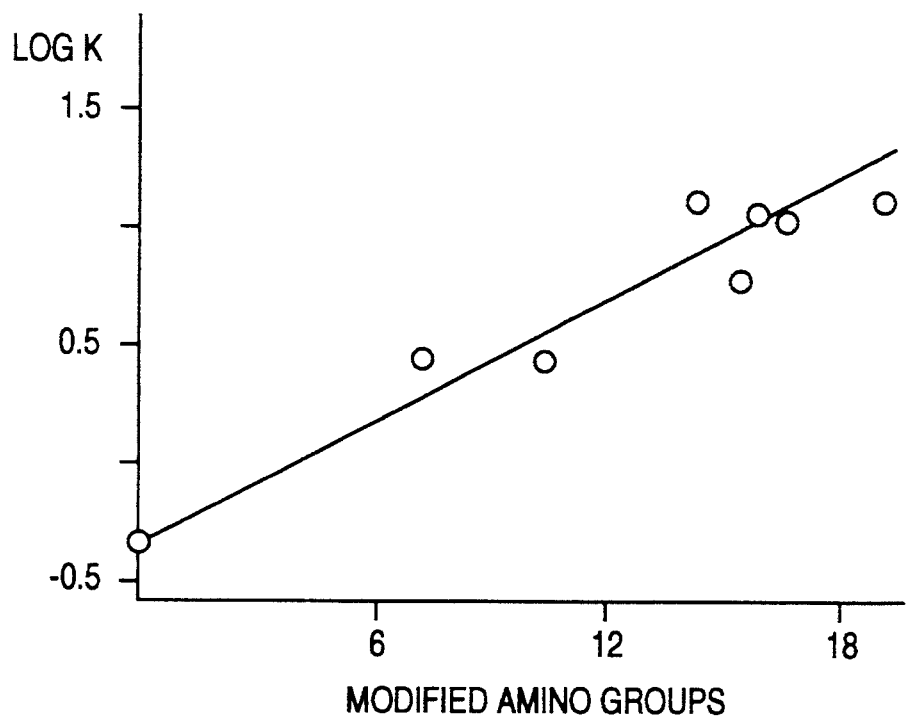
FIG. 3 is a graph of Log K versus the number of modified amino groups for PEGylated BSA.

To establish the quantitative relationship between the partition coefficient, K, and the degree of modification, the latter was measured by the reduction in primary amines in the relationship between the log of the partition coefficient and the degree of substitution of the amino groups over the range studied (0.-30% modification) (FIG. 3; r=0.96, p<0.001).

Brooks et al (45) have predicted that K for the modified protein ($K_{pL}$) should be related to K of both free protein ($K_p$) and ligand ($K_L$) as well as the number of attached polymer molecules (n). They gave the equation $K_{pL}=K_p.K_L^n$, which can be expressed as follows:

$$\log K_{pL} = \log K_p + n \log K_L$$

A linear relationship between log of partition coefficient for the modified protein and the number of molecules of ligand attached is then predicted with a slope and intercept of log $K_L$ and log $K_p$, respectively.

From FIG. 3, the intercept was found to be −0.36 in good agreement with the experimental value of −0.39±0.09 (mean±SD, n=5) for the log K of the unmodified albumin. However, the slope (log $K_L$) was 0.08, much less than the experimental value obtained by independent measurement of the partitioning of PEG ($^{14}$C-PEG-4000) in the phase system (log K=0.4±0.002, mean±SD, n=3). Such a discrepancy between the experimental and the calculated partition coefficient for the MPEG is unlikely to be due to overestimation of the number of modified amino groups since this would have to be an overestimation of 80% to produce the results obtained here.

Sharp et al. (1) have measured the partition coefficient of MPEG-IgGs modified to different extents and noted that if the Brooks equation was used to calculate the number of MPEG molecules attached to the protein on the basis of partition coefficient this markedly underestimated the value obtained when this was measured directly by using a MPEG labelled with $^{14}C$. These authors did not however establish the relationship between substitution and Log K.

EXAMPLE 2

DEMONSTRATION OF THE HETEROGENEITY OF MPEG-MODIFIED ALBUMIN BY COUNTER-CURRENT DISTRIBUTION

Having demonstrated the relationship between the partition coefficient of albumin and the degree of modification with MPEG we used multiple partitions (i.e. counter-current distribution, CCD) to analyse chromatographically the MPEG-albumin.

Figure 4:
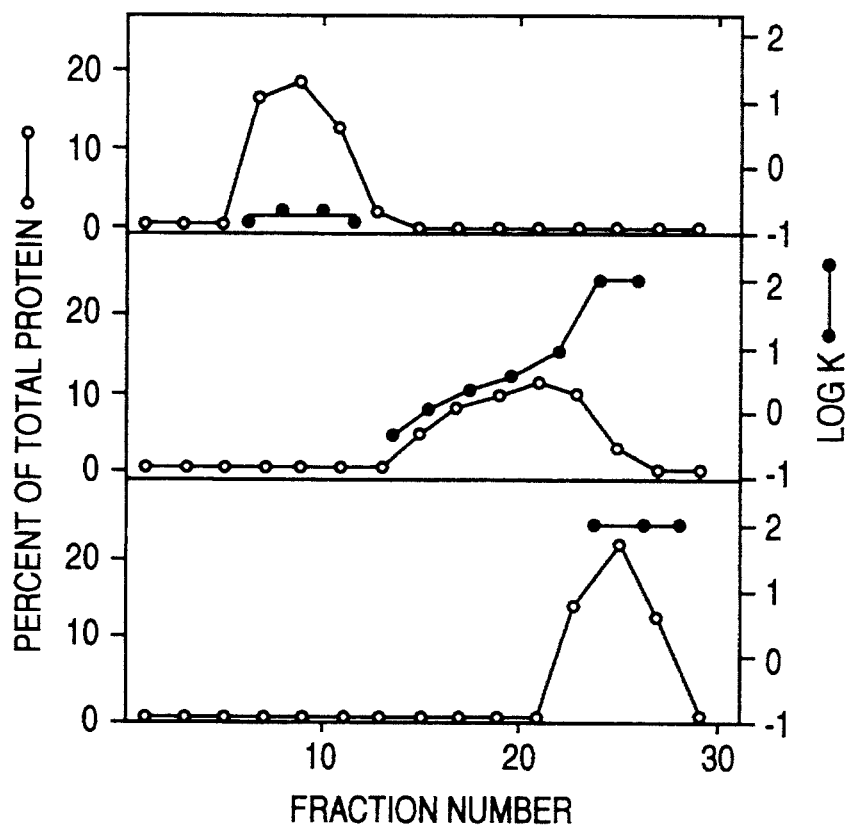
FIG. 4 shows CCD profiles of albumin and MPEG-modified albumins 1 and 2.

FIG. 4 shows CCD profiles of albumin, MPEG-modified albumins 1 & 2. These two last were obtained by incubation of albumin with TMPEG by using TMPEG:lys molar ratios of 2 to 1 and 16 to 1, respectively. Partition coefficients for the protein present in each fraction are also shown.

Unmodified albumin is distributed between fractions 7 and 13, to the left of the CCD train (FIG. 4 top). The position of the distribution peak on the left hand side of the CCD train means albumin partitions in favour of the bottom phase of the biphasic system (i.e. low partition coefficient), in agreement with the observations in single tube partitioning (FIGS. 1 and 2). The constant value for the partition coefficient of the unmodified albumin all along the distribution peak (FIG. 4, top) is consistent with homogeneity of the protein preparation.

MPEG-albumin$_1$ shows a CCD profile between fractions 14 and 26 (FIG. 4, middle) towards the right of that for unmodified albumin (Fractions 7-15, FIG. 4, top). This result reflects the higher partition coefficient obtained in single tube partitions for modified albumin compared with unmodified albumin (FIGS. 1 and 2). The partition coefficient of albumin present in any of the fractions between fractions 14 and 26 was higher than that for the unmodified albumin (FIG. 4, middle and top). Furthermore, the former partition coefficients were not constant as in the case of unmodified albumin, but increased progressively from the left-hand side to the right-hand side of the distribution profile (FIG. 4, middle). Because of the relationship between the partition coefficient and the degree of modification (FIG. 3), this heterogeneity of partitioning indicates that MPEG-albumin consists of a mixture of albumins modified with MPEG to different extents. Consequently, mixtures of MPEG-modified albumins can be fractioned by counter-current distribution on the basis of the degree of modification.

The CCD profile for MPEG-modified albumin$_2$ (TMPEG: Lys molar ratio of 16 to 1), which showed the highest partition coefficient in single tubes (FIG. 2), were located towards the right of the CCD train, between fractions 23 and 28 (FIG. 4, bottom). The partition coefficient of albumin present in these fractions (FIG. 4, bottom) was higher than those corresponding to albumin in fractions 1 to 23 (FIG. 4, top and middle). It should be noted that MPEG-modified albumins located in fractions 24 and 26 have the same partition coefficient independently of being present in either the complex MPEG-albumin$_1$, (FIG. 4, middle) or MPEG-albumin$_2$ (FIG. 4, bottom).

Using the equation defining the relationship between log K and degree of substitution calculated from the regression of FIG. 3 (log K = 0.084xn − 0.36) the extent of modification (n) can be estimated for the individual fractions (table II).

TABLE II

| Fraction | log K | Calculated No. of NH$_2$ modified* |
|---|---|---|
| MPEG-albumin$_1$, (FIG. 4, middle) | | |
| 14 | −0.38 | 0 |
| 16 | 0.024 | 4.6 |
| 18 | 0.33 | 8.2 |
| 20 | 0.52 | 10.5 |
| 23 | 0.90 | 15.0 |
| 25 | 2.00 | 28.1 |
| 27 | 2.00 | 28.1 |
| MPEG-albumin$_2$ (FIG. 4, bottom) | | |
| 25 | 2.00 | 28.1 |
| 27 | 2.00 | 28.1 |
| 29 | 2.00 | 28.1 |

*Note this estimate will have to be corrected if there is significant heterogeneity of chain length in the TMPEG preparation used, since this influences partition coefficient of the PEG-protein adducts (1).

EXAMPLE 3

DEMONSTRATION THAT THE PARTITIONING BEHAVIOUR OF SOME MPEG-PROTEINS DEVIATES FROM THE BEHAVIOUR ILLUSTRATED FOR MPEG-BSA IN EXAMPLE 1

The protein granulocyte-macrophage colony stimulating factor gm-CSF was coupled to MPEG as described for albumin. To generate PEG-gm-CSF complexes with different degrees of substitution by PEG, a range of PEG:lysine molar ratios was used for the coupling reaction (10:1 to 1000:1). This protein has 6 lysines so that species with 1 to 6 substitutions are theoretically possible. Commercially labelled gm-CSF-I$^{125}$ (Amersham) which is biologically active was used for these experiments. The FPLC profiles of similar experiments in which the molar ratio was changed (see Example 4 below) establish that progressive substitution does take place with increasing molar ratios.

Figure 5:
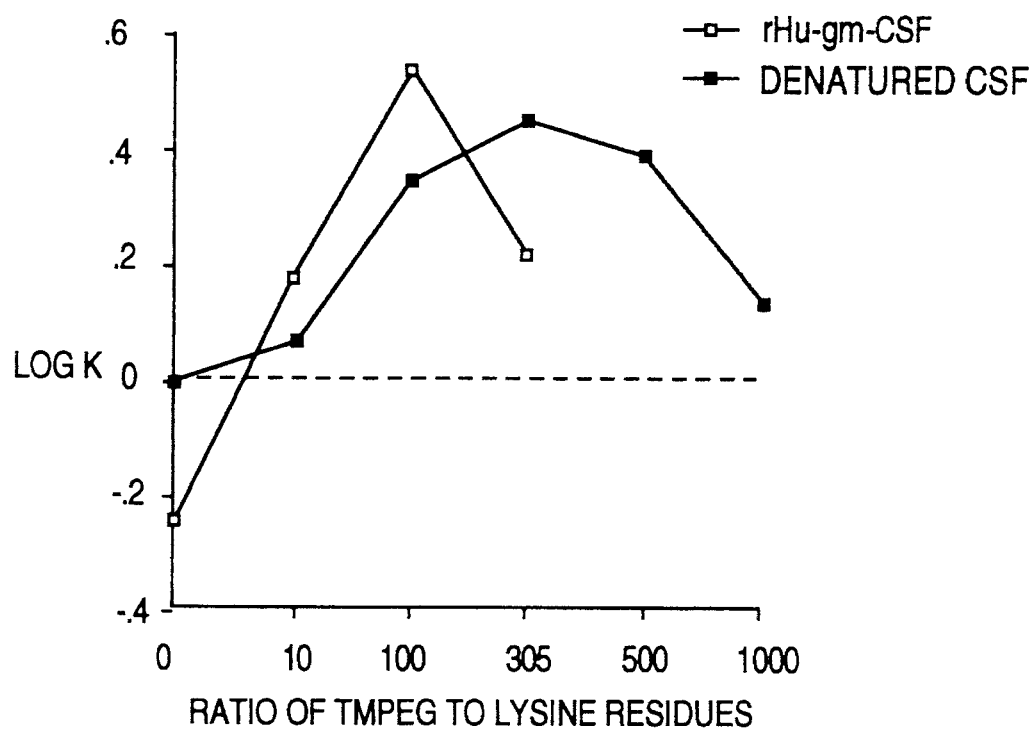
FIG. 5 is a graph of Log K versus TMPEG: Lys residues for recombinant human gm-CSF and denatured CSF.
Figure 6A:
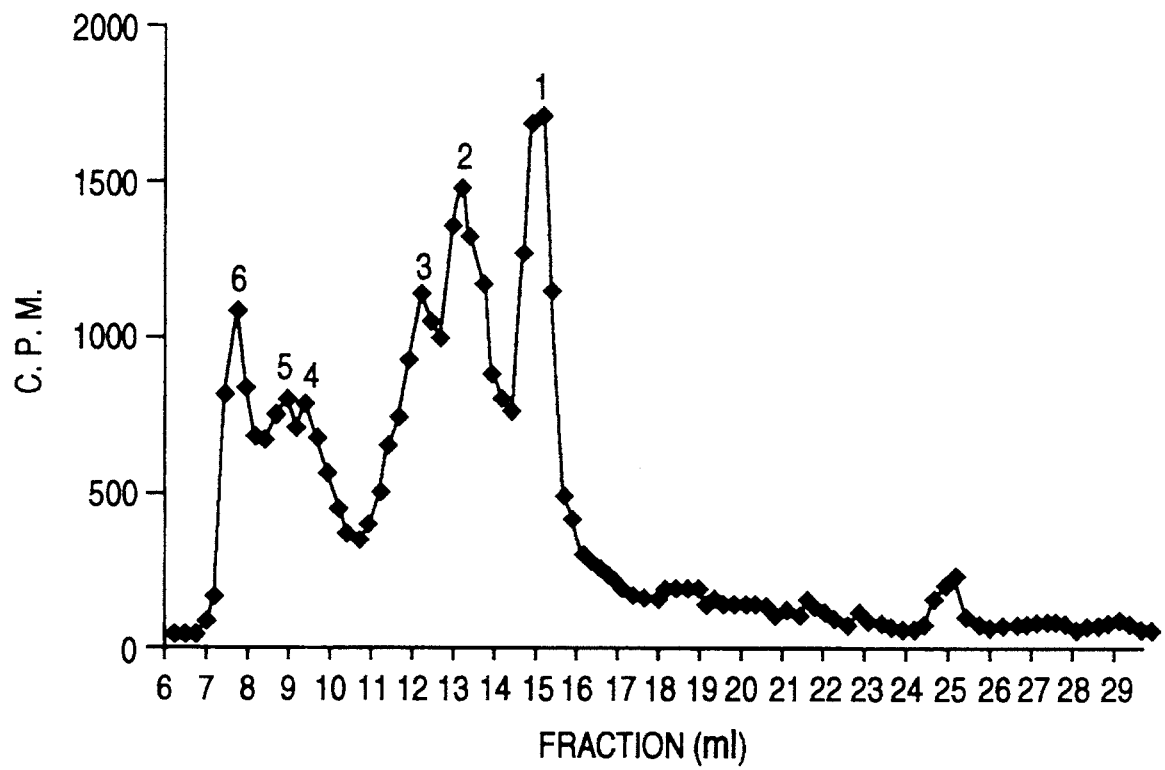
FIG. 6A (upper panel) shows the amount of label eluted in various fractions when PEGylated recombinant human gm-CSF was submitted to FPLC.

With increasing molar ratios, log K increases and then falls (FIG. 5). This demonstrates that, unlike BSA, the expected log linear relationship predicted by the Brooks equation does not follow. In the same experiment gm-CSF denatured by boiling had a reduced log K, suggesting that conformational changes in the protein had altered surface properties in such a way as to reduce partitioning to the PEG phase. With this material there was a more pronounced increase in K at lower molar ratios. This presumably reflects greater ease of PEG-modification due to the more open structure of the denatured protein (this suggestion is apparently confirmed by FPLC where PEGylation at 305:1 TMPEG:lysine produces a larger high molecular weight peak with denatured gm-CSF (FIG. 6A and B).

Although this may seem a disadvantage of the method, it should be noted:

1) that the K values did not fall below that for the unmodified protein (thus still potentially allowing CCD separation).

2) with the non-denatured material the fall in K occurs only when the protein is subjected to very high molar ratios (not those in the range likely to be used to produce biologically active PEG-gm-CSF).

3) alternative methods, FPLC and PAGE, were not superior in performance to CCD (see below).

EXAMPLE 4

DEMONSTRATION OF THE PRODUCTION OF HETEROGENEOUS MODIFIED PRODUCTS AT SINGLE MOLAR RATIOS OF TMPEG TO LYSINE FOR GM-CSF

Representative experiments are shown in FIGS. 7A1, A2 and A3 and 7B1, and B2 in which gm-CSF was exposed to a range of molar ratios of TMPEG to lysine. FPLC reveals that with the exception of the lowest molar ratios, where only a very small proportion of the material is modified (on a single lysine on the basis of the shift in apparent molecular weight, cf. Katre's experience with PEG-IL2 (19)), the material is heterogeneous. Even though FPLC is used here to demonstrate heterogeneity there are several disadvantages of the method (see below).

This example demonstrates that the problems of achieving uniformly modified PEG-protein complexes are not confined to large proteins with many lysines such as albumin.

EXAMPLE 5

DISADVANTAGES OF FPLC AND PAGE THAT EMPHASISE THE NEED FOR THE NEW METHOD

Figure 8A:
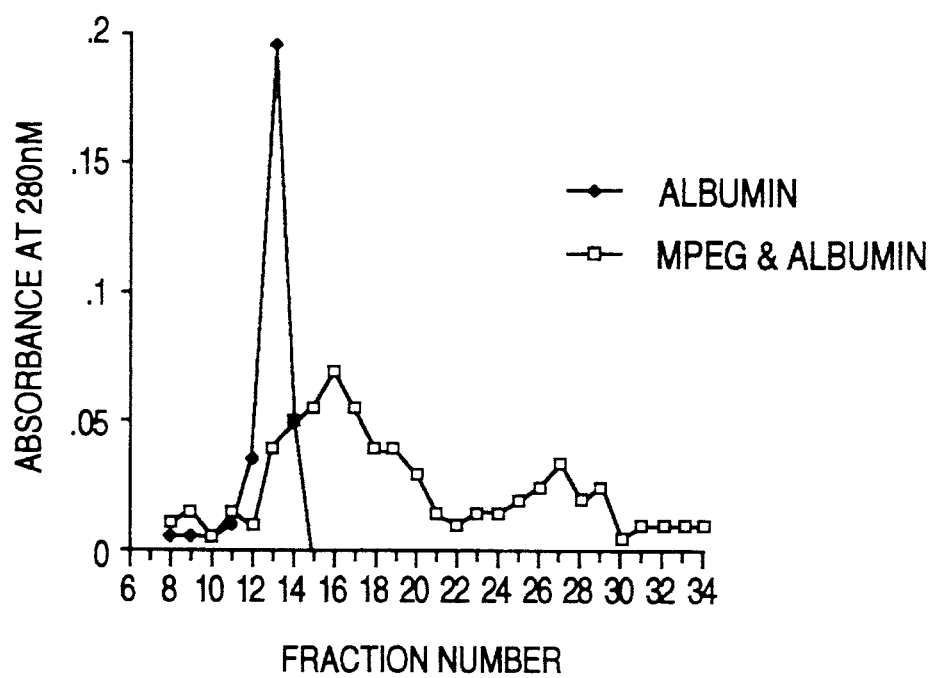
FIG. 8A shows the result of FPLC of protein PEGylated with contaminated TMPEG containing MPEG.

1) Demonstration that Progressive Ageing of TMPEG Yields PEG-Cytokine Complexes That Do Not Resolve on FPLC We have found that MPEG induces a non-specific broadening effect with a change to slow elution, in FPLC profiles of proteins including BSA (FIG. 8A) and gm-CSF. This is relevant to an observation made on FPLC profiles of TMPEG modified gm-CSF. We noted that as batches of TMPEG become older there is not only reduced activity as indicated by reduction in the number of modified species obtained at the same molar ratio of TMPEG to lysine, but also a progressive loss of resolution on FPLC profiles, accompanied by a reduced elution rate (FIG. 8B1, B2, B3 and B4). As tresyl groups are lost or become inactive, preparations are effectively contaminated with MPEG or an equivalent (unreactive TMPEG) and this, in view of the findings of FIG. 8A, may explain the above observation.

Figure 9A:
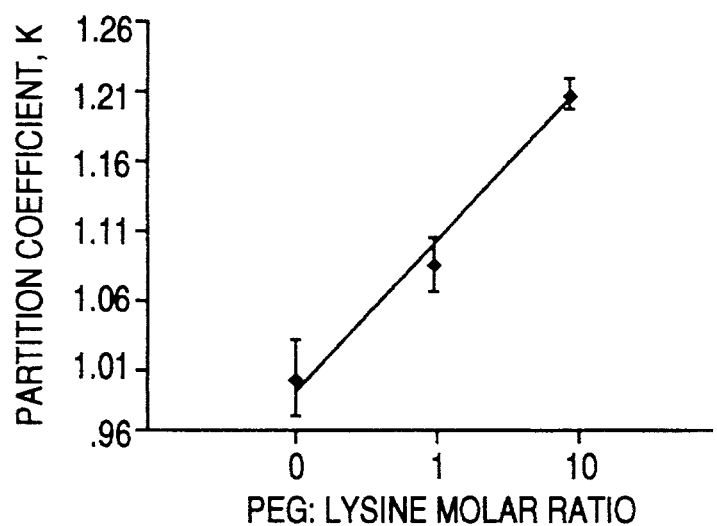
FIG. 9A shows the effect of TMPEG treatment on phase partitioning of recombinant human gm-CSF.
Figure 9B:
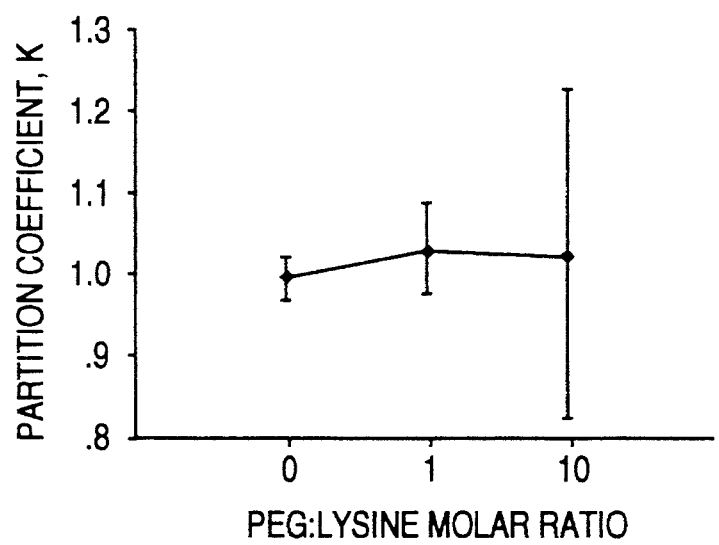
FIG. 9B shows the lack of effect of MPEG treatment on phase partitioning of recombinant human gm-CSF.

Since uncoupled PEG (MPEG) does not significantly influence partitioning (FIG. 9B shows the lack of effect on $I^{125}$-gm-CSF) we can state that inactive TMPEG or MPEG will not, in contrast to its adverse influence on FPLC, affect partitioning methods such as CCD.

Figure 10A:
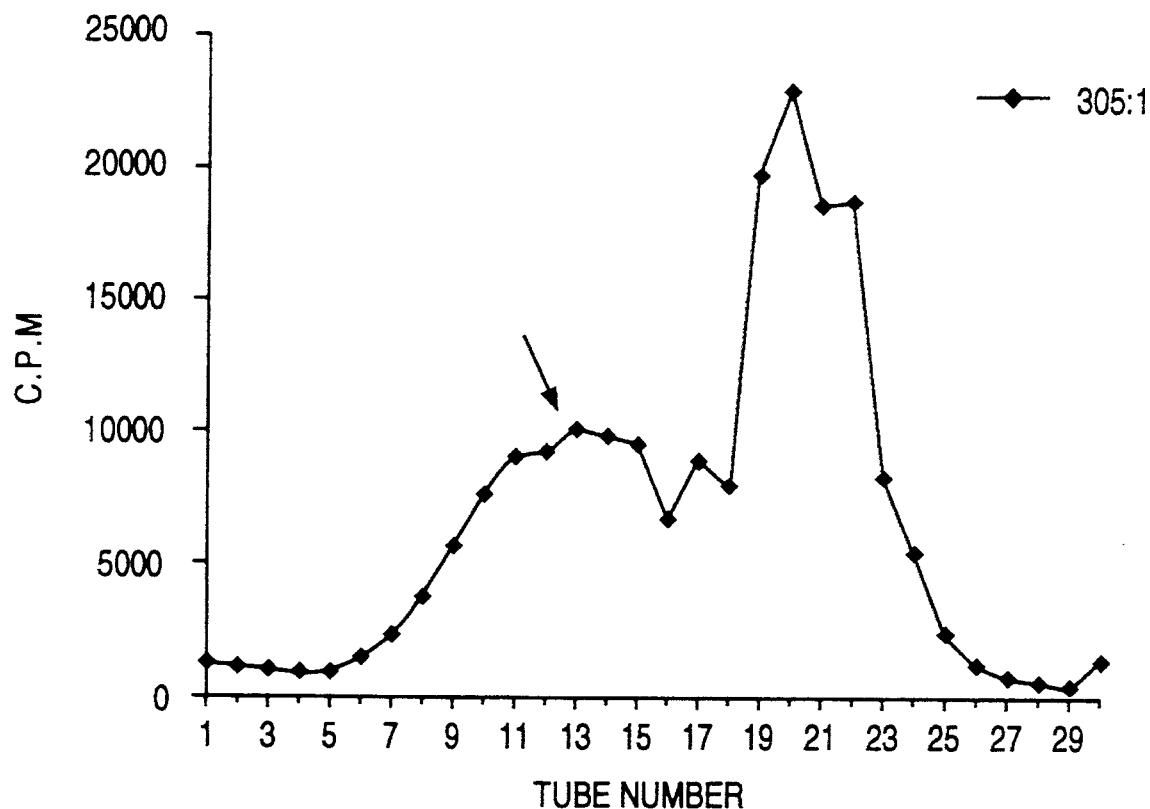
FIG. 10A shows the results of CCD on recombinant human gm-CSF exposed to an aged (19 week old) sample of TMPEG at a TMPEG:lysine molar ratio of 305:1.
Figure 10B:
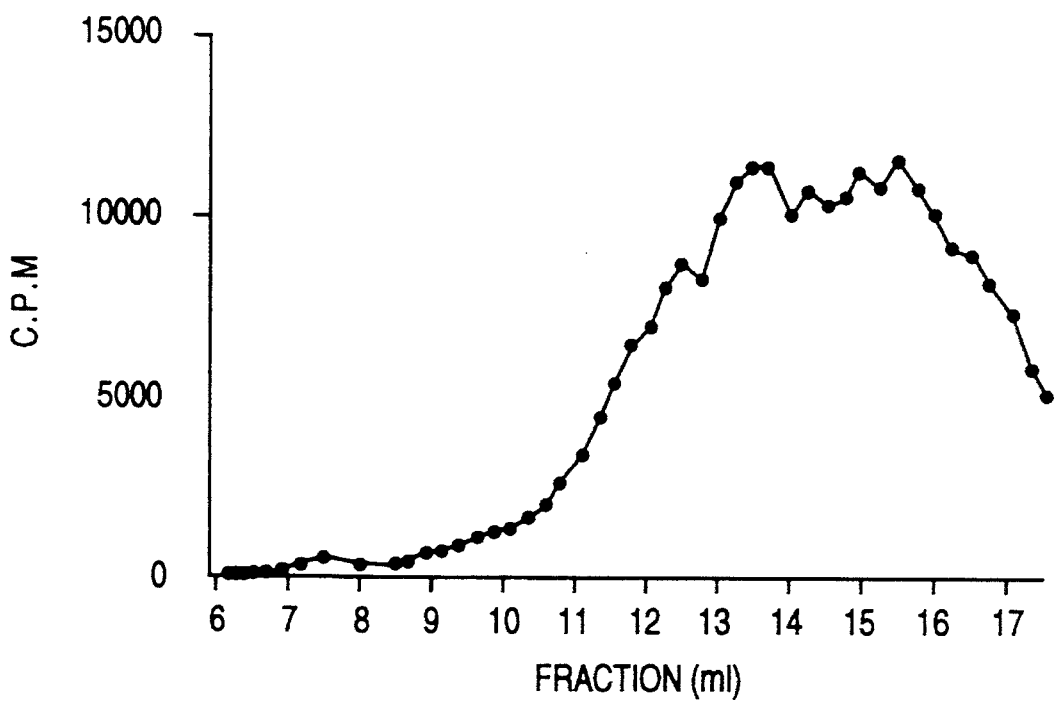
FIG. 10B shows the result of FPLC on recombinant human gm-CSF exposed to an aged (19 week old) sample of TMPEG at a TMPEG:lysine molar ratio of 305:1.

FIGS. 10A and B show that with CCD there is a clear discrimination of modified material from unmodified whereas with FPLC with an "aged" TMPEG preparation there was considerable overlap, and no clear resolution between modified and unmodified material.

In addition to this point, the finding with MPEG and FPLC indicate that if FPLC is required, the choice of neutralisation strategy should be considered. Albumin will yield PEG-albumin, lysine will yield a PEG derivative containing a carboxyl group, hydroxylamine will produce a PEG molecule with a terminal hydroxyl group. The effect of each neutralisation product needs to be examined with the specific PEG-protein being manufactured.

2) Apparent molecular Weights on FPLC and PAGE of PEG-modified Proteins Do Not Relate Simply to Degree of Modification.

Figure 11:
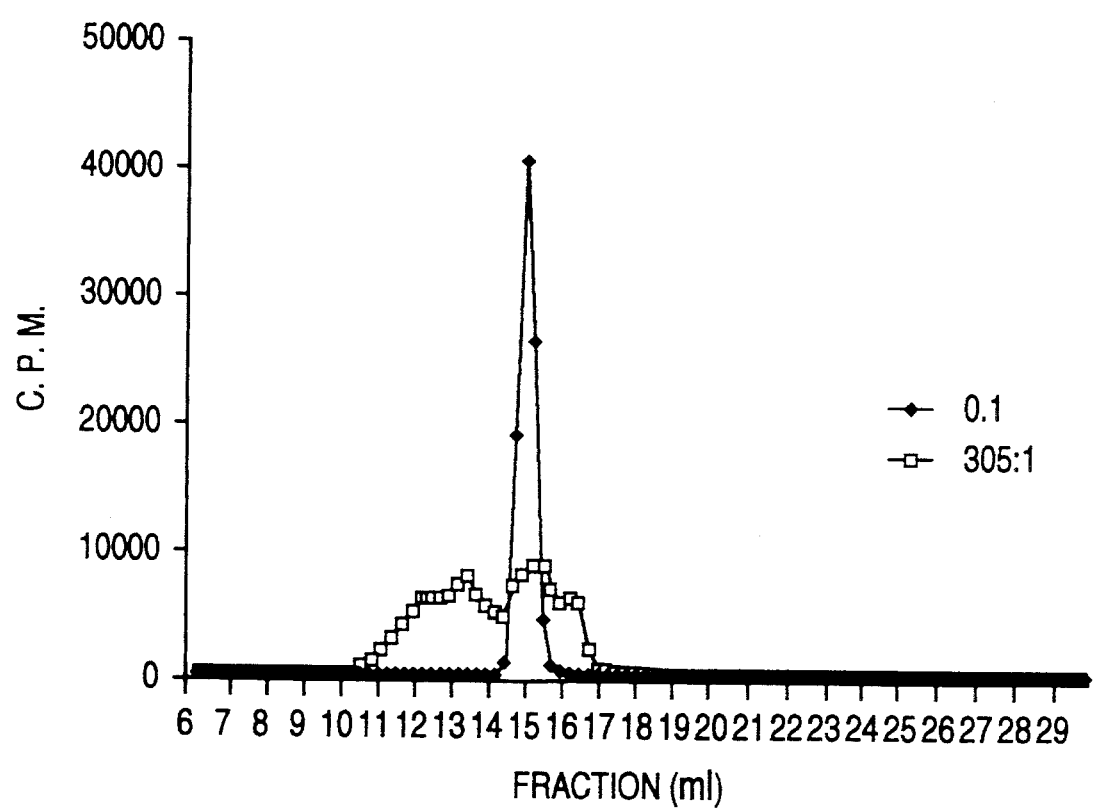
FIG. 11 shows fractionating of PEGylated and unmodified recombinant human gm-CSF.

In all experiments using TMPEG:lysine ratios sufficient to modify most of the protein molecules (e.g. of 305:1 or more), modified gm-CSF eluted both faster and slower than the unmodified material (FIG. 11a and b).

Figure 12:
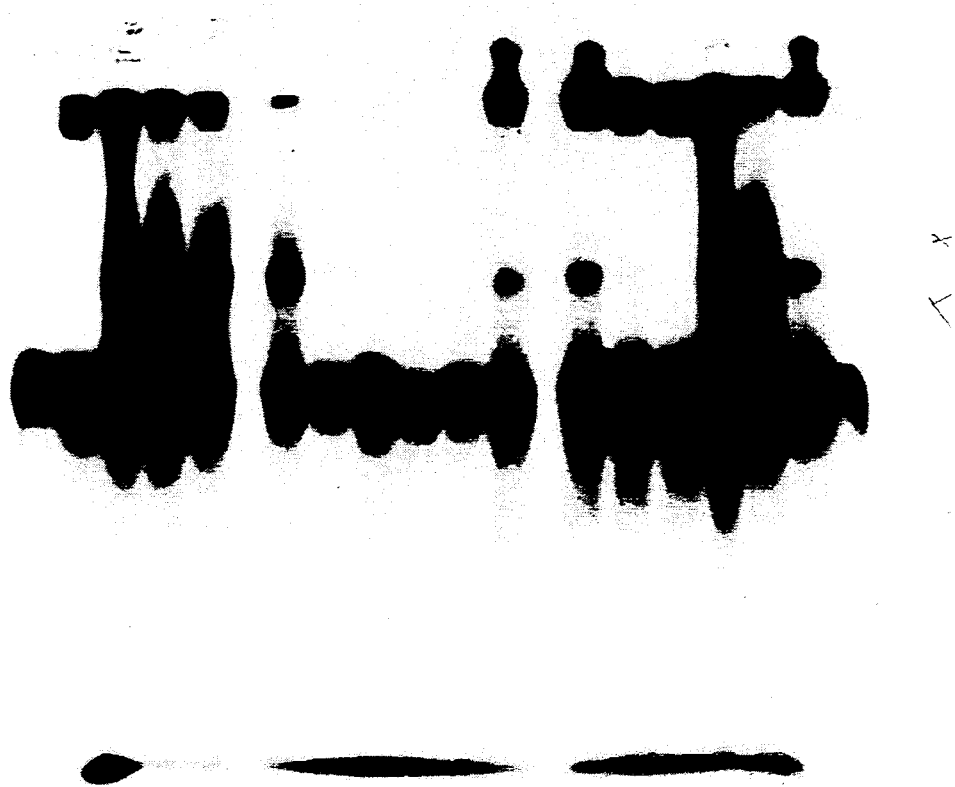
FIG. 12 shows polyacrylamide gel electrophoresis of unmodified and PEGylated recombinant human gm-CSF.

Similar results were obtained with polyacrylamide gel electrophoresis (FIG. 12), where for both native and denatured rHu-gmCSF (lanes 12,14–16,19,20), the modification results in material running both before and after the unmodified band. However, this experiment demonstrates that unlike FPLC, PAGE is not detrimentally influenced by MPEG.

This demonstrates that the degree of modification, specifically the number of lysine residues modified by PEG, difficult to infer from either method.

3) FPLC Can Conceal Heterogeneity of the PEG-protein Product

Although, to some extent FPLC reveals the heterogeneity of the product (cf. Example 4), as demonstrated below in Example 6, CCD reveals heterogeneity even in material with apparently simple profiles on FPLC.

EXAMPLE 6

CCD DEMONSTRATES HETEROGENEITY OF MODIFIED MATERIAL, EVEN WHEN NOT OBVIOUS ON THE BASIS OF FPLC

Figure 13A:
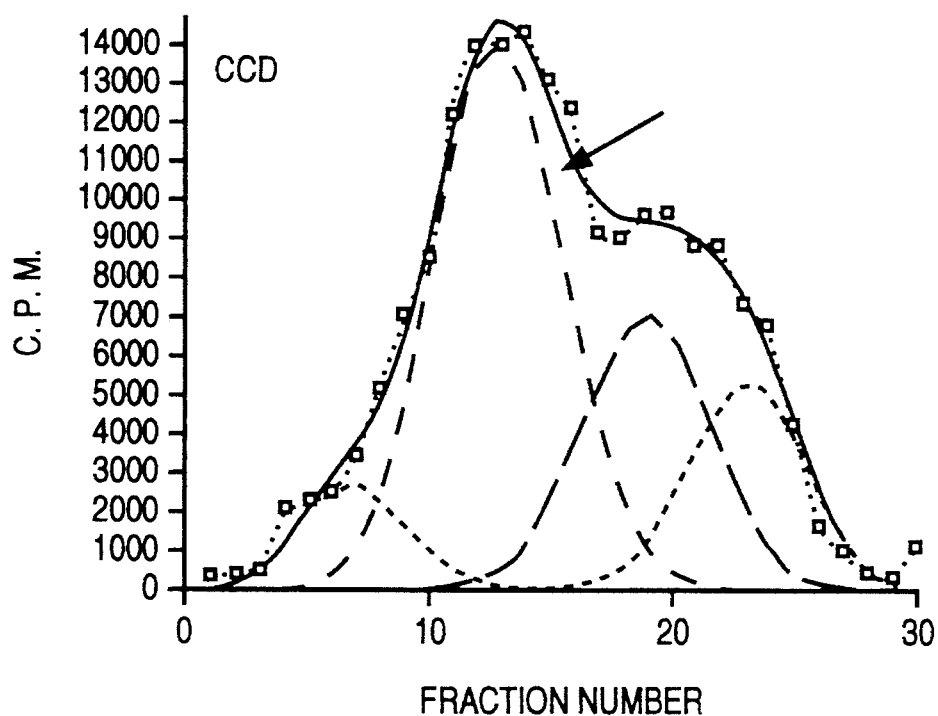
FIG. 13A (upper panel) shows the result of CCD on recombinant human gm-CSF exposed to TMPEG:lysine at a molar ratio of 10:1.

Counter current distribution profiles, analysed by a curve fitting algorithm, allow calculation of the number of species (in this case various PEG-gm-CSF complexes) present. Comparison of the FPLC and CCD profiles in FIG. 13A and B, shows that the latter can reveal heterogeneity not prominent on the former.

The added benefit of being able to perform CCD on a large scale are pertinent to the industrial production of PEG-proteins.

EXAMPLE 7

DEMONSTRATION THAT GM-CSF MODIFIED TO DIFFERENT EXTENTS HAS VARIED BIOLOGICAL ACTIVITY

Samples were taken from FPLC fractions of a modified sample (prepared at TMPEG:lysine 305:1), eluting a) faster than, b) with and c) slower than the unmodified material. Gm-CSF has many different biological activities; we chose to use its priming of f-met-leu-phe induced neutrophil oxidative burst activity (assessed by nitroblue tetrazolium reduction). Fractions were exposed to human peripheral blood neutrophils with FMLP in microtitre plates.

Figure 14:
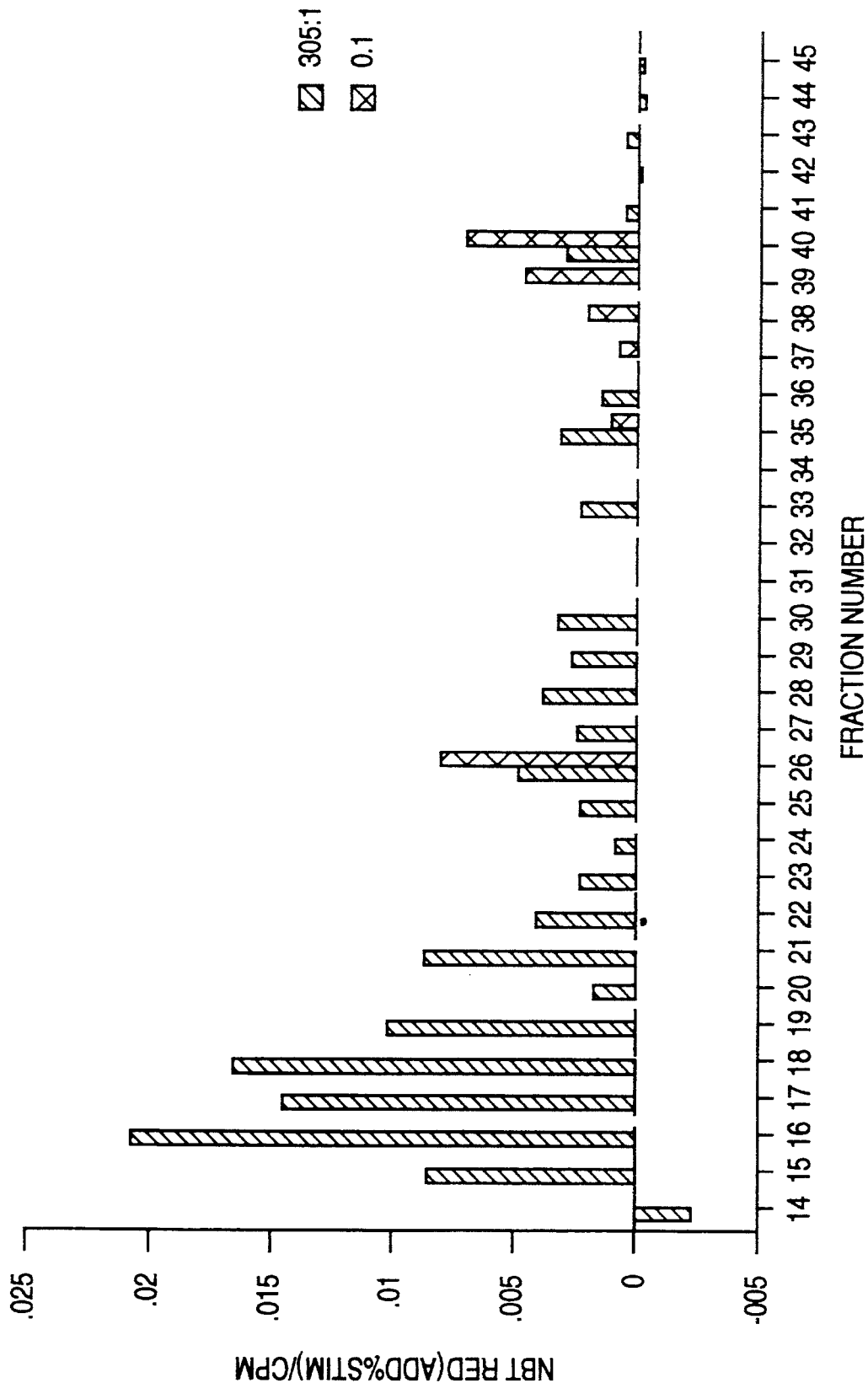
FIG. 14 shows neutrophil priming activity of recombinant human gm-CSF.

The biological activity of the fractions was normalised with respect to the protein by means of the radioactivity (using $I^{125}$ labelled gm-CSF, Amersham). Fractions ranged from no biological activity to 3–6 times the activity seen in fractions from the peak of unmodified material from an identical FPLC fractionation (FIG. 14).

This example illustrates the need for precise control of, or fractionation of, the PEG-protein species being produced to achieve the desired biological activity.

METHODS

1) FPLC

Samples were analysed on Pharmacia FPLC system with a Superose-12 column previously equilibrated with coupling buffer. 200 ul of the samples were loaded on to the column and then eluted with coupling buffer at a flow rate of 0.3 mls per minute; 0.25 ml fractions were collected.

Elution buffers varied, e.g. for some applications coupling buffer (0.05M sodium phosphate pH7.% containing 0. 125M NaCl) was used. Where cells were to be exposed directly to eluate, phosphate buffered saline pH 7.3 and circa 285mOsm was used. Proteins were detected by absorption at wavelength 280 mm if sufficiently abundant, or by detection of radio-label ($I^{125}$).

2) SDS GEL ELECTROPHORESIS (PAGE)

15% polyacrylamide gel was used with a stacking gel. Samples were mixed with equal volume of loading buffer and then the resultant mixture was denatured by placing in a water-bath at 100° C. for 1 minute. 40 ul of the denatured mixture was loaded per well and electrophoresis was carried out at 150 Volts; maximum current. The gel was dried onto Whatman No 1 filter paper and the gel was then autoradiographed at 70° C. with a rare earth intensifying screen. The film was developed e.g. after a 4 day exposure.

2) NBT reduction test

Polymorphonuclear leucocytes (PMN) were isolated using the differential centrifugation method of Eggleton et al (J.Immunol. Methods 121(1989)105-113). The cell concentration used was $1\times10^7$ per ml in Hanks balanced salt solution (HBSS). FMLP (SIGMA) was dissolved in dimethyl sulfoxide (DMSO, BDH) and used in a final concentration of $1\times10^{-7}M$ in $1\times10^{-2}\%$ DMSO. The test solutions were aliquoted (30 ul) and filled into the wells of a microtitre plate (96 wells per plate, NUNC) in triplicates.

50 ul of HBSS containing 5.25% of fetal calf serum was added to each well. The plates were warmed to 37° C. and 25 ul of prewarmed HBSS containing PMN was added. The cells were incubated for 2 hours for priming. 100 ul of prewarmed NBT solution (nitro blue tetrazolim grade III, SIGMA, 0.1% w/v) containing FMLP was added to each well (the latter triggering NBT reduction). The reaction was stopped after 15 minutes on ice. Processing was done according to a modification of the method described by Rock (J.Immunol. Methods 82(1985)161-167). The plates were centrifuged (1000 rpm, 6 min) and the supernatant was removed. After air drying for 3 min 250 ul of 70% methanol was added. After centrifugation and removing of the supernatant the cells were lysed with 100 ul of 2M KOH. 12 hours later 125 ul of DMSO was added to each well. Colorimetry was performed on a Titertek Multiscan reader (Flow Labs) set to Mode Abs 2 with Filter 7(620 nm) and Filter 3(450 nm).

LEGENDS TO ADDITIONAL FIGURES

FIG. 5 Phase-partitioning of $I^{125}$ labelled recombinant human gm-CSF (rHu-gmCSF) was performed in a PEG/dextran system after TMPEG exposure to biologically active and denatured (boiled) protein. For both preparations, log K is curvilinear with respect to the coupling ratio (TMPEG:lysine). The latter determines the degree of modification (number of lysine groups reacted).

Figure 6B:
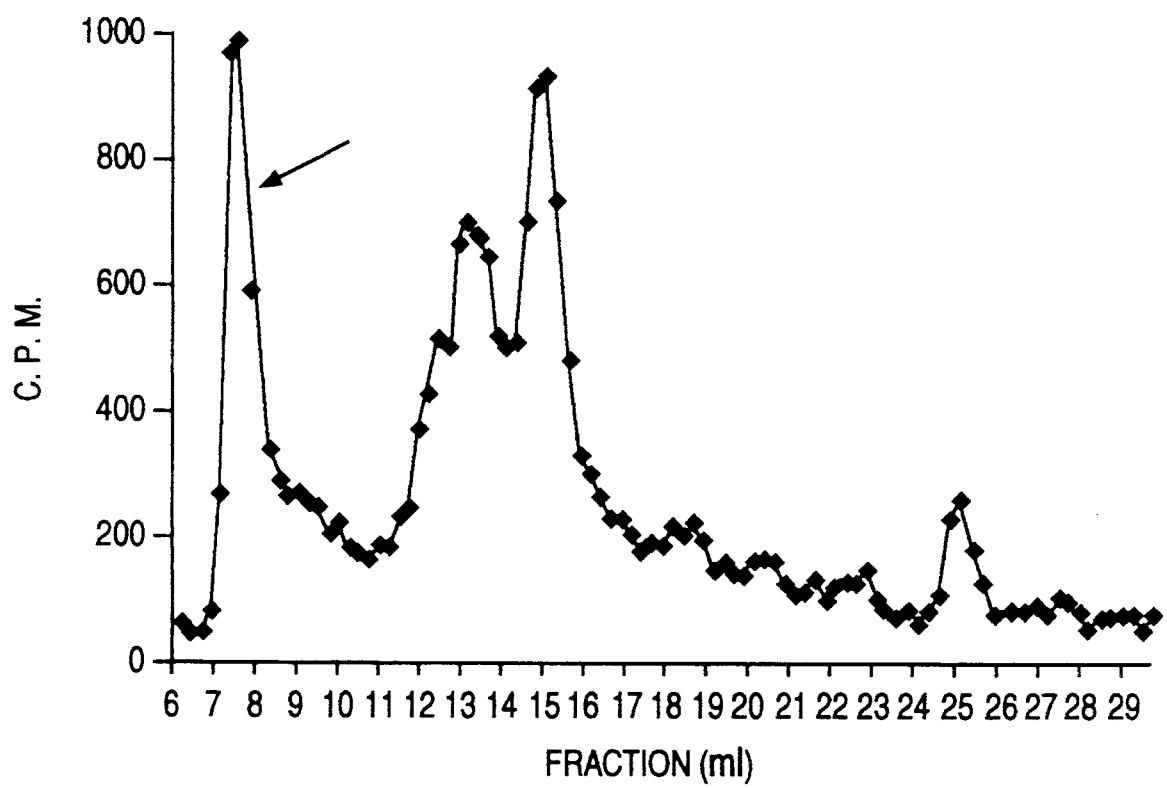
FIG. 6B (lower panel) shows the amount of label eluted in various fractions when denatured (boiled) gm-CSF-$^{125}$I was submitted to FPLC.

FIG. 6A-6B Boiling (FIG. 6B, lower panel) prior to TMPEG exposure of rHu-gmCSF at a TMPEG:lysine ratio of 305:1, increased the FPLC peak at the highest molecular weight (arrow). It reduced intermediate peaks 4 and 5 with respect to the unboiled control (FIG. 6A, Upper panel).

FIG. 7A1-7B2 FPLC of two different batches of rHu-gmCSF-$I^{125}$.

| A1: | Upper panel: | unmodified rHu-gmCSF: |
|---|---|---|
| A2: | Middle panel 305:1 | TMPEG:lysine molar ratio. |
| A3: | Lower panel 1000:1 | " |
| B1: | Upper panel 10:1 | " |
| B2: | Lower panel 305:1 | " |

FIG. 8A-8B4 a) Exposure of MPEG to proteins prior to FPLC produces a broadening of profiles that could potentially interfere with FPLC of TMPEG modified proteins, if samples are contaminated with MPEG or inactivated TMPEG.

b) Use of progressively older TMPEG (stored at room temperature under desiccation), significantly alters the FPLC profiles of the modified protein in FIGS. 8B1-8B4.

FIG. 9A-9B

Comparison of the influence of TMPEG (FIG. 9A, upper panel) and MPEG exposure (FIG. 9B, lower panel) on the partitioning behaviour of rHu-gmCSF. The latter produces no significant increment in K.

FIG. 10A-10B

Figure 13B:
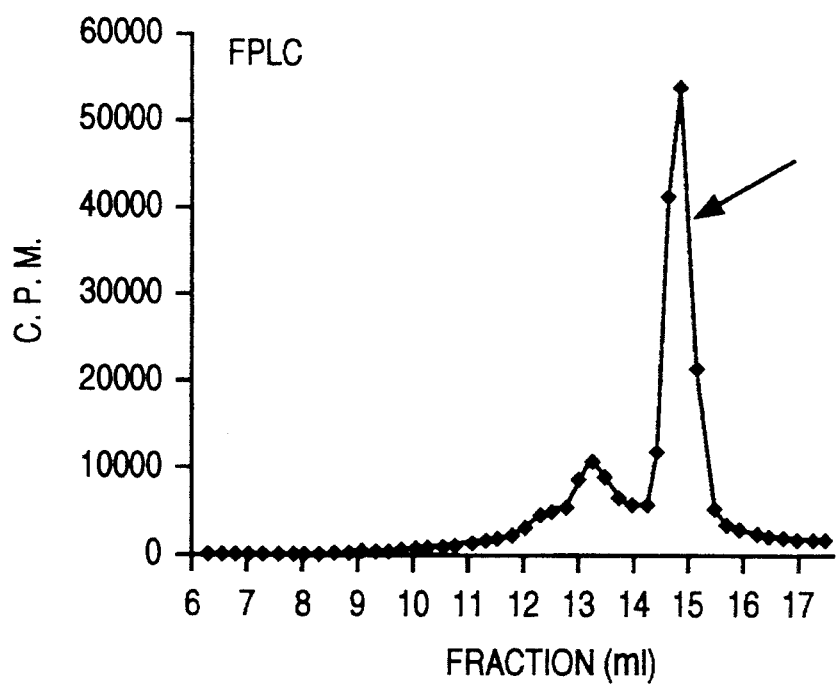
FIG. 13B (lower panel) shows the result of FPLC on recombinant human gm-CSF exposed to TMPEG:lysine at a molar ratio of 10:1.

Comparison of CCD (FIG. 10A, upper panel) and FPLC (FIG. 13B, lower panel) on rHu-gm-CSF exposed an aged (19 week old) sample of TMPEG at a TMPEG:lysine molar ratio of 305:1. Only the CCD successfully discriminated between modified and unmodified (arrowed) peaks.

FIG. 11

PEG modified rHu-gmCSF (exposed to 305:1 TMPEG:lysine) runs both faster and slower than the unmodified material, demonstrating that no clear relationship between apparent molecular weight and number of lysine residues modified by PEG exists on FPLC.

FIG. 12

Poly acrylamide gel electrophoresis of unmodified and PEG modified rHu-gmCSF exposed to various molar ratios of TMPEG:lysine. lanes: 1=unmodified; 2=denatured; 3=exposed to TMPEG:lysine of 1000:1; 4=500:1; 5=305:1; 6=markers; 7=100:1; 8=10:1; 9=0:1; 10=MPEG:lysine of 305:1; 11=10:1; 12=denatured rHu-gmCSF modified at 100:1; 15=10:1; 16=0:1; 17=rHu-gm CSF modified at 1000: 1; 18=rHu-gmCSF modified at 305:1; 19=denatured rHu-gmCSF modified at 305:1; 20=denatured rHu-gmCSF 0:1.

FIG. 13A-13B

CCD (FIG. 13A, upper panel) and FPLC (FIG. 13B, lower panel) on rHu-gmCSF exposed to only 10:1TMPEG:lysine. Whereas FPLC shows only a small peak of unmodified material the CCD profile demonstrates heterogeneity more clearly. The CCD profile has been fitted by a computer program (Blonquist and Wold, Acta Chem Scand B28,56:1974) and reveals 3 curves in addition to that in the location of the unmodified material (arrowed).

FIG. 14

Neutrophil priming activity of rHu-gm-CSF measured by NBT reduction (see text) and normalised for the amount of protein present by expressing with respect to $I^{125}$ (c.p.m.) per fraction.

Fractions from FPLC of unmodified (crosshatched) and 305:1 modified rHu-gm-CSF (hatched) allow comparison of biological activity. The modified material contains species with no activity and with higher activity than unmodified material.

REFERENCES

1). Sharp, K, A., Yalpini, M., Howard, S. J. and Brooks, D. E. (1986). Anal Biochem. 154, 110–117.
2). Stocks, S. J., Jones, A. J. M., Ramey, C. W. and Brooks, D. E. (1986). A fluorimetric assay of the degree of modification of protein primary amines with polyethylene glycol. Anal. Biochem. 154, 232–234.
3). Abstracts in Biocommerce (1988) 10 (3):abstract 24769.
4). Abstracts in Biocommerce (1988) 10(3):abstract 24770.
5). Abstracts in Biocommerce (1988) 10(3):abstract 24771.
Abstracts in Biocommerce (1988) 10(3):abstract 24772.
8). Ho, D. H., Brown, N. S., Yen, A., Holmes, R., Keating M., Abuchowski, A., Newman, R. A. and Krakoff, I. H. (1986). Clinical pharmacology of polyethylene glycol-L-asparaginase. Drug Metabolism 14, 349–352.
9). Abuchwski, A., Davis, F. F. and Davis, S. (1981). Immunosuppresive properties and circulating life of Achromobacter glutaminase-asparaginase covalently attached to polyethylene glycol in man. Cancer Treatment Reports, 65, 1077–1081.
10). Davis, S., Park, Y. K., Abuchowski, A. and Davis, F. F. (1981). Hypouricaemic effect of polyethyleneglycol modified urate oxidase. Lancet, 281–283.
11). Abuchowski, A., van Es, T., Palczuk, N. C., McCoy, J. R. and Davis, F. F. (1979). Treatment of L5178V tumor-bearing BDFI mice with a nonimmunogenic L-glutaminase-L-asparaginase. Cancer Treatment Reports 63, 1127–1132.
12). Bendich, A., Kafkeewitz, D., Abuchowski, A. and Davis, F. F. (1982). Immunological effects of native and polyethylene glycol-modifies asparaginase from Vibrio succinogenes and Escherichisa coli in normal and tumour-bearing mice. Clin. exp. Immunol, 48, 273–278.
13). Sacova, K. V., Abuchowski, A., van Es, T., Davis, F. F. and Paczuk, N. C. (1979). Preparation of a nonimunogenic argianse by the covalent attachment of polyethylene glycol. Biochim. Biophys. Acta 578, 47–53.
14). Beauchamp, C. O., Gonias, S. L., Menapace, D. P. and Pizzo, S. V. (1983). A new procedure for the synthesis of polyethylene glycol-protein adducts; effects on function, receptor recognition, and clearance of superoxide dismutase, lactoferrin, and 2-macroglobulin. Anal. Biochem. 131, 25–33.
15). Rajagopaian, S., Gonias, S. L. and Pizzo, S. V. (1985). A nonantigenic covalent streptokinase-polyethylene glycol complex with plasminogen activator function. J. Clin Invet 75, 413–419.
16). Davis, S., Abuchowski, A., Park, Y. K. and Davis, F. F. (1981). Alteration of the circulating life and antigenic properties of bovine adenosine deaminase in mice by attachment of polyethylene glycol. Clin. exp. Immunol. 46, 649–652.
17). Kamisaki, Y., Wada, H., Yagura, T., Matsushima, A. and Inada, Y. (1981). Reduction in the immunogenicity and clearance rate of Escherichia coli L-asparaginase by modification with monomethoxypolyethylene glycol. J. Pharmacol. Exp. Therap. 216, 410–414.
18). Hershfeld, M. J., Buckley, R. H., Greenberg, M. L., Melton, A. L., Schiff, R., Hatem, C., Kurtzberg, J., Markert, M., Kobayashi, R. H., Kobayashi, A. L. and Abuchowski, A. (1987). Treatment of adenosine deaminase deficiency with polyethylene glycol-modified adensine deaminase. New Eng. J. Med. 316, 589–596.
19). Katre, N. V., Knauf, M. J. and Laird, W. J. (1987). Chemical modification of recombinant interleukin 2 by polyethylene glycol increases its potency in the murine Meth A sarcoma model. Proc. Nat. Acad. Sci. 84, 1487–1491.
20). Chen, R. H.-L., Abuchowski, A., van Es, T., alczuk, N. C. and Davis, F. F. (1988). Properties of two urate oxidases modified by the covalent attachment to poly(ethylene glycol). Biochim. Biophys. Acta 660, 293–298.
21). Lisi P. L., van Es, T., Abuchowski, A., Palczuk, N. C. and Davis, F. F. (1982). Enzyme therapy 1. Polyethylene glycol:B-glucuronidase conjugates as potential therapeutic agents in acid mucopolysaccharidosis.
22). Abuchowski, A. and Davis, F. F. (1979). Preparation and properties of polyethylene glycol-trypsin adducts. Biochim. Biophys. Acta 578, 41–46.
23). Wieder, K. J., Palczuk, N. C., van Es, T. and Davis, F. F. (1979). Some properties of polyethylene glycol:-phenylalanine ammonia-lyase adducts. J. biol. Chem. 254, 12579–12587.
24). Suzuki, T., Kanbara, N., Tomono, T., Hayashi., No and Shinohara, I. (1984). Physicochemical and biological properties of poly(ethylene glycol)-coupled immunoglobulin G. Biochim. Biophys Acta 788,248–255.
25). Veronese, F. M., Largajolli, R., Boccu, E., Benassi, C. A. and Schiavon, O. (1985). Surface modification of proteins. Activation of monomethoxy-polyethylene glycols by phenylchloroformates and modification of ribonulease and superoxide dismutase. Applied Biochem. Biotechnol. 11, 141–152.
26). Davis, F. F., Abuchowski, A., van Es, T., Palczuk, N. C., Sacova, K., Chen, H.-L. and Pyatak, P. (1980). Soluble, nonantigenic polythylene glycol-bound enzymes. In "Biomedical Polymers. Polymeric Materials and Pharmaceuticals for Biomedical Use" (Ed E. P. Goldberg and A. Nakajima) pp 441–452. Academic Press, N.Y.
27). Harris, J. M. (1985). Laboratory synthesis of polyethylene glycol derivatives. Rev. Macromol. Chem. Phys. C25, 325–373.
28). Nilsson, K. and Mosbach, K. (1981). Immobilization of enzymes and affinity ligands to various hydroxyl group carrying supports using highly reactive sulfonyl chlorides. Biochem. Biophys. Res. Commun. 102,449–457.
29). Nilsson, K. and Mosbach, K. (1984). Immobilization of ligands with organic sulfonyl chlorides. Methods in Enzymology 104, 56–69.
30). Delgado, C., Francis, G. E. and Fisher, D. (1988a). Coupling of PEG to proteins by activation with tresyl chloride. Applications in immunoaffinity cell partitioning. In "Advances in Separations Using Aqueous Phase Systems in Cell Biology and Biotechnology" (Ed D Fisher and I A Sutherland), Plenum Press, to be published.

31). Vadhan-Raj S, LeMaistre A, Keating M et al. (1987). Effects of recombinant human granulocyte-macrophage colony stimulating factor in patients with malignancy and in patients with bone marrow failure (abstract) Blood 70,144a.

32). Gabrilove J, Jakubowski A, Fain K et. al. (1987). A phase I/II study of rhG-CSF in cancer patients at risk for chemotherapy induced neutropenia (abstract). Blood 70:135a.

33). Morstyn G, Duhrsen U, Campbell L, et. al. Granulocyte-colony stimulating activity in patients with advanced cancer receiving melphalan (abstract). Blood 70, 140a.

34). Francis G. E. & Pinsky C. (1987). Clinical trials of differentiation inducing agents: Current trials and future prospects. Chapter in Proceedings of the Second Conference on Differentiation Therapy. Ravens Press, in Press (copy enclosed).

35). Francis G. E. & Pinsky C. (1987). Growth and differentiation control. In Cancer Cemotherapy and Biological Response Modifiers Annual 9. Eds. H. M. Pinedo, B. A. Chabner and D. L. Longo. Elsevier Science Publishers B. V., in press.

36). Stocks, S. J., Jones, A. J. M., Ramey, C. W. and Brooks, D. E. (1986) Anal. Biochem. 154,232–234.

37). Habeed, A.S.F.A. (1966) Anal. Biochem. 14,328–336.

38). Bradford, M. N. (1976) Anal. Biochem. 72, 248–254.

39). Johansson, G. (1985) in partitioning Aqueous Two-Phase Systems, Theory, Methods, Uses and Applications to Biotechnology (Walter, H., Brooks, D. E. and Fisher, D. eds.) pp. 161–226, Academic Press, New York.

40). Treffry, T. E., Sharpe, P. T., Walter, H. and Brooks, D. E. (1985) in Partitioning in Aqueous Two-Phase Systems, Theory, Methods, Uses and Applications to Biotechnology (Walter. H., Brooks, D. E. and Fisher, D. eds) pp 132–148 Academic Press, New York.

41). Peters, T. Jr. (1972) in The Plasma Proteins (Putnam, F. W. ed.) 2nd ed., Vol. 1 pp 140–142. Academic Press.

42). Albertson P.-A. (1985). Partition of Cell Particles and Macromolecules. 3rd ed. Wiley, Interscience, New York.

43). Flanagan, S. D. and Barondes, S. H. (1975) J. Biol. Chem. 250, 1484–1489.

44). Harris, J. M. (1985) Rev. Macromal. Chem. Phys. C25, 325–373.

45). Brooks, D. E., Sharp, K. A. and Fisher, D. (1985) in Partitioning in Aqueous Two-Phase Systems, Theory, Methods, Uses and Applications to Biotechnology (Walter, H., Brooks, D. E. and Fisher, D., eds.) pp 11–84, Academic Press, New York.

We claim:

1. A process for fractionating a mixture of polyethylene glycol (PEG)-protein adducts having different degrees of PEG substitution comprising:
   (a) partitioning the PEG-protein adducts in a PEG-containing aqueous biphasic system according to the degree of PEG substitution, and
   (b) recovering a PEG-protein adduct of predetermined degree of PEG substitution from one phase of the biphasic system.

2. The process according to claim 1 wherein the PEG-protein adduct is an adduct of monomethoxyPEG.

3. The process according to claim 1 wherein the monomethoxyPEG adduct is formed by reaction of the protein with 2,2,2-trifluoroethanesulfonyl monomethoxy polyethylene glycol (TMPEG).

4. The process according to claim 3 wherein unreacted TMPEG is destroyed or the adduct-forming reaction is quenched by addition of lysine or albumin.

5. The process according to claim 1 wherein partitioning is performed batchwise.

6. The process according to claim 1 wherein partitioning is performed continuously.

7. The process according to claim 6 wherein partitioning is performed by counter-current flow of the two phases.

8. The process according to claim 1 wherein the protein is granulocyte-macrophage colony stimulating factor (gm-CSF).

9. The process of claim 2 wherein the protein is granulocyte-macrophage colony stimulating factor (gm-CSF).

* * * * *